United States Patent [19]

Linz et al.

[11] Patent Number: 5,489,693

[45] Date of Patent: Feb. 6, 1996

[54] CYCLIC IMINO DERIVATIVES, PHARMACEUTICAL COMPOSITIONS CONTAINING THESE COMPOUNDS AND PROCESSES PREPARING THEM

[76] Inventors: Guenter Linz, Erlenweg 8, W-7951 Mittelbiberach; Volkhard Austel, Kapellenweg 7, W-7950 Biberach 1; Frank Himmelsbach, Ahornweg 16, W-7951 Mittelbiberach; Johannes Weisenberger, Haydnweg 5, W-7950 Biberach 1; Thomas Mueller, Alter Postplatz 17, W-7590 Biberach 1; Helmut Pieper, Kappelenweg 5, W-7950 Biberach 1; Elke Seewaldt-Becker, Huehnerfeldstrasse 26, W-7950 Biberach 1, all of Germany

[21] Appl. No.: 52,877

[22] Filed: Apr. 26, 1993

[30] Foreign Application Priority Data

Apr. 28, 1992 [DE] Germany .......................... 42 13 931.7

[51] Int. Cl.⁶ .................... C07D 207/38; A61K 31/40
[52] U.S. Cl. .................... 548/550; 548/250; 548/251; 548/252; 548/253; 548/254; 548/543; 548/551; 554/60; 554/141; 546/281
[58] Field of Search ................... 548/543, 550, 548/250, 251, 252, 253, 254, 543, 550, 551; 514/822, 424, 92, 227.8, 235.5, 343, 381, 422; 544/60, 141; 546/281

[56] References Cited

U.S. PATENT DOCUMENTS 4,491,591  1/1985  Abrahams ........................ 424/274

5,123,954  6/1992  Moriyasu et al. ................. 548/543

FOREIGN PATENT DOCUMENTS

| 0196184 | 10/1986 | European Pat. Off. . |
| 0350437 | 1/1990 | European Pat. Off. . |
| 0409163 | 1/1991 | European Pat. Off. . |
| 0528369 | 2/1992 | European Pat. Off. . |
| 477626 | 4/1992 | European Pat. Off. . |
| 0503548 | 9/1992 | European Pat. Off. . |
| 0525629 | 2/1993 | European Pat. Off. . |
| 2247166 | 2/1990 | Japan . |

*Primary Examiner*—Allen J. Robinson
*Assistant Examiner*—Brian Bembenick
*Attorney, Agent, or Firm*—Robert P. Raymond; Alan R. Stempel; Mary-Ellen M. Devlin

[57] ABSTRACT

Cyclic imino derivatives of the formula

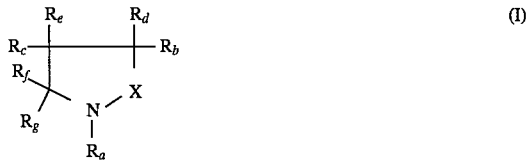

(I)

wherein X and $R_a$ to $R_g$ are as defined herein, useful for their inhibitory effects on aggregation, pharmaceutical compositions containing the compounds and processes for preparing them.

5 Claims, No Drawings

CYCLIC IMINO DERIVATIVES, PHARMACEUTICAL COMPOSITIONS CONTAINING THESE COMPOUNDS AND PROCESSES PREPARING THEM

The invention relates to cyclic imino derivatives of the general formula

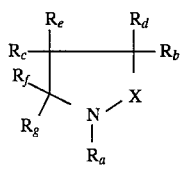

(I)

the stereoisomers, mixtures and the salts thereof, particularly the physiologically acceptable addition salts thereof with inorganic or organic acids or bases, which have valuable pharmacological properties, preferably aggregation-inhibiting effects, pharmaceutical compositions containing these compounds and processes for preparing them.

In general formula I above, one of the groups $R_a$ or $R_b$ denotes an A—B— group and the other group $R_a$ or $R_b$ denotes an F—E—D— group, wherein A denotes an amino group, an aminoalkyl group having 1 to 4 carbon atoms in the alkyl moiety, an amidino or guanidino group, whilst in the above-mentioned amino, aminoalkyl, amidino or guanidino groups an amino or imino group may be substituted by a $C_{1-4}$-alkyl group or by a group which can be cleaved in vivo and an amino group may additionally be substituted by another $C_{1-4}$-alkyl group or by an aralkyl group, B denotes a phenylene group which may be substituted by a fluorine, chlorine or bromine atom, by one or two alkyl groups, by a trifluoromethyl, hydroxy, alkoxy, alkylsulphenyl, alkylsulphinyl, alkylsulphonyl, nitro, $(R_1)_2N$-, N-alkylcarbonyl-$NR_1$- or N-alkanesulphonyl-$NR_1$- group, in which $R_1$ denotes a hydrogen atom or an alkyl or aralkyl group, a pyridinylene, pyrimidinylene, pyrazinylene, pyridazinylene or triazinylene group, each of which may be alkyl-substituted in the carbon skeleton and in which additionally one or two —CH=N— groups may each be replaced by a —CO—$NR_1$— group, wherein $R_1$ is as hereinbefore defined and there must be at least 2 carbon atoms between the nitrogen atom of the —CO—$NR_1$— group and the nitrogen atom of the group A or of the cyclic imino group to which the group B is linked, a 1,3-pyrrolidinylene, 1,3-piperidinylene, 1,4-piperidinylene, 1,3-hexahydroazepinylene, 1,4-hexahydroazepinylene, 1,4-piperazinylene or 1,4-homopiperazinylene group which may be linked to group A or to the cyclic imino group via position 1, but the link may not be made via a nitrogen-nitrogen bond, and a $C_{5-7}$-cycloalkylene group in which a methylene group may be replaced by an —$NR_1$— group wherein $R_1$ is as hereinbefore defined, whilst additionally there must be at least two carbon atoms between the nitrogen atom of the —$NR_1$— group and a nitrogen atom of the group A or of the cyclic imino group, and an indanylidene, 1,2,3,4-tetrahydronaphthylidene or 5H-benzocycloheptenylidene group or A and B together denote a pyrrolidinyl, piperidinyl, hexahydroazepinyl or piperazino group optionally substituted in the 1-position by the group $R_1$ or by a group which can be cleaved in vivo, whilst $R_1$ is as hereinbefore defined, D denotes a phenylene group which may be substituted by a fluorine, chlorine or bromine atom, by one or two alkyl groups, by a trifluoromethyl, hydroxy, alkoxy, alkylsulphenyl, alkylsulphinyl, alkylsulphonyl, nitro, $(R_1)_2N$-, N-alkylcarbonyl-NR $_1$-, N-alkanesulphonyl-$NR_1$-, carboxymethoxy or alkoxycarbonylmethoxy group, wherein $R_1$ is defined as hereinbefore, a C5-7-cycloalkylene group, a pyridinylene, pyrimidinylene, pyrazinylene, pyridazinylene or triazinylene group, each of which may be alkyl-substituted in the carbon skeleton, whilst additionally a —CH=N— group may be replaced by a —CO—$NR_2$—) group ,(wherein $R_2$ denotes a hydrogen atom, an alkyl or aralkyl group or a bond with the group E) if there are at least two carbon atoms between a heteroatom of the group E or the nitrogen atom of the cyclic imino group to which the group D is linked and the nitrogen atom of the —$CONR_2$-group, a 1,3-pyrrolidinylene, 1,3-piperidinylene, 1,4-piperidinylene, 1,3-hexahydroazepinylene or 1,4-hexahydroazepinylene, 1,4-piperazinylene or 1,4-homopiperazinylene group which may be linked via position 1 to the group E or to the cyclic imino group and in which a methylene group adjacent to the nitrogen atom may be replaced by a carbonyl group, but the link must not be via a nitrogen-nitrogen bond, a $C_{5-7}$-cycloalkylene group in which a methylene group is replaced by an —$NR_1$— group, wherein $R_1$ is as hereinbefore defined, E denotes a straight-chained or branched $C_{1-5}$-alkylene group optionally substituted by a hydroxy, alkoxy, $(R_1)_2N$-, alkyl-CO-$NR_1$-, aralkyl-CO-$NR_1$-, aryl-CO-$NR_1$-, $C_{1-5}$-alkyl-$SO_2$-$NR_1$-, arylalkyl-$SO_2$-$NR_1$-, aryl-$SO_2$-$NR_1$-, $(R_1)_2N$-CO-$NR_1$-, alkoxy-CO-$NR_1$- or aralkoxy-CO-$NR_1$-group, wherein the $R_1$ groups which may be identical or different are as hereinbefore defined, a straight-chained or branched $C_{2-5}$-alkenylene group, whilst in a $C_{2-4}$-alkylene group the methylene group linked to the group D may be replaced by an oxygen or sulphur atom, by a sulphinyl, sulphonyl, imino, alkylimino, aralkylimino, alkylcarbonylimino, aralkylcarbonylimino, arylcarbonylimino, alkanesulphonylimino, arylalkanesulphonylimino, arylsulphonylimino, carboxymethylimino, alkoxycarbonylmethylimino or aralkoxycarbonylmethylimino group, and F denotes a group which can be metabolised in vivo to form a carboxyl group, or it denotes a carboxyl group, a sulpho, phosphono, O-alkylphosphono or tetrazol-5-yl group, and either (a) X denotes a methylene or carbonyl group, $R_d$ and $R_e$ together denote another carbon-carbon bond, $R_c$ denotes a hydrogen atom, a $C_{1-5}$-alkyl group, an aryl group, a hydroxy group, a straight-chained or branched $C_{1-5}$-alkoxy group, whilst a $C_{1-3}$-alkoxy group may be substituted in the 1-, 2- or 3-position by a carboxy, alkoxycarbonyl, aminocarbonyl, alkylaminocarbonyl, dialkylaminocarbonyl, cycloalkylaminocarbonyl, cycloalkylalkylaminocarbonyl, piperidinocarbonyl, morpholinocarbonyl, thiomorpholinocarbonyl, 1-oxidothiomorpholinocarbonyl or 1,1-dioxidothiomorpholinocarbonyl group, or $R_c$ may denote an aralkoxy, alkylamino, dialkylamino, aralkylamino, N-alkyl-aralkylamino, arylamino, N-alkyl-arylamino, pyrrolidino, piperidino or hexamethyleneimino group, whilst the methylene group in the 4-position of a piperidino group may be replaced by an oxygen or sulphur atom, or by a sulphinyl, sulphonyl, imino, alkylimino, aralkylimino, alkylcarbonylimino, aralkylcarbonylimino, arylcarbonylimino, alkanesulphonylimino, arylalkanesulphonylimino or arylsulphonylimino group, $R_f$ denotes a hydrogen atom, a straight-chained or branched $C_{1-5}$-alkyl group, an aralkyl or aryl group and $R_g$ denotes a hydrogen atom or an alkyl group or (b) X denotes a carbonyl, group, $R_c$ and $R_e$ together with the carbon atom between them denote a carbonyl group, $R_d$ denotes an alkyl group optionally substituted by an aryl, carboxy, alkoxycarbonyl, aminocarbonyl, alkylaminocarbonyl, dialkylaminocarbonyl, cycloalkylaminocarbonyl, cycloalkylalkylaminocarbonyl, piperidinocarbonyl, morpholinocarbonyl, thiomorpholinocarbonyl, 1-oxidothiomorpholinocarbonyl or 1,1-dioxidothiomorpholinocarbonyl group, $R_f$ denotes a hydrogen atom, an alkyl or aryl group and $R_g$ denotes a hydrogen atom or an alkyl group or (c) X denotes a methylene group, $R_f$ and $R_g$ together with the carbon atom between them denote a carbonyl group, $R_c$ denotes a hydrogen atom or, if B or D denotes a 1,3-pyrrolidinylene, 1,3-piperidinylene, 1,4-piperidinylene, 1,3-hexahydroazepinylene, 1,4-hexahydroazepinylene, 1,4-piperazinylene or 1,4-homopiperazinylene group linked to the cyclic imino group via position 1, $R_c$ may also denote an aryl group and $R_d$ and $R_e$ each denote a hydrogen atom or together denote another carbon-carbon bond or (d) X denotes a methylene or carbonyl group and $R_c$ to $R_f$ may each denote a hydrogen atom, whilst the term "a group which can be metabolised in vivo to produce a carboxyl group" and "a group which can be cleaved in vivo" denote, for example, an ester group of the formulae

—CO—OR',

—CO—O—(HCR")—O—CO—R"'and

—CO—O—(HCR")—O—CO—OR"', wherein

R' denotes a straight-chained or branched alkyl group having 1 to 6 carbon atoms, in which the methyl group may be substituted by an $(R_1)_2$NCO- group (wherein $R_1$ is as hereinbefore defined), by a pyridyl, cycloalkylaminocarbonyl, cycloalkylalkylaminocarbonyl, pyrrolidinocarbonyl, piperidinocarbonyl, morpholinocarbonyl, thiomorpholinocarbonyl, 1-oxidothiomorpholinocarbonyl or 1,1-dioxidothiomorpholinocarbonyl group or a $C_{1-3}$-alkyl group may be substituted in the 1-, 2- or 3-position by an aryl group or in the 2- or 3-position by a pyrrolidin-2-on- 1-yl, morpholino, thiomorpholino, 1-oxidothiomorpholino or 1,1-dioxidothiomorpholino group, or R' may denote a $C_{1-4}$-alkenyl group, a cycloalkyl, cycloalkenyl, cycloalkylalkyl, methoxymethyl or cinnamyl group, R" denotes a hydrogen atom or an alkyl group and R"' denotes a straight-chained or branched $C_{1-6}$-alkyl group or a cycloalkyl, cycloalkylalkyl or arylalkyl group, whilst a carboxyl group thus formed after cleaving may, if it is bound to a nitrogen atom of the group A, be decarboxylated, thereby releasing the amino or imino group, and, unless otherwise specified, the term "an alkyl group" as used above denotes a straight-chained or branched $C_{1-3}$-alkyl group, "a cycloalkyl group" denotes a $C_{5-7}$-cycloalkyl group, "a cycloalkenyl group" denotes a $C_{5-7}$-cycloalkenyl group, "an alkoxy group" denotes a straight-chained or branched $C_{1-3}$-alkoxy group and "an aryl group" denotes a phenyl group which may be mono-, di- or trisubstituted by fluorine, chlorine or bromine atoms, by $C_{1-5}$-alkyl groups, by hydroxy, alkoxy, phenylalkoxy, trifluoromethyl, mercapto, alkylsulphenyl, alkylsulphinyl, alkylsulphonyl, amino, alkylamino, dialkylamino, alkylcarbonylamino, phenylalkylcarbonylamino, phenylcarbonylamino, alkoxycarbonylamino, alkylsulphonylamino, phenylsulphonylamino, N-alkylcarbonyl-alkylamino, N-phenylalkylcarbonyl-alkylamino, N-phenylcarbonylalkylamino, N-alkoxycarbonyl-alkylamino, N-alkylsulphonylalkylamino, N-phenylsulphonyl-alkylamino, cyano, aminocarbonyl, alkylaminocarbonyl, dialkylaminocarbonyl, aminosulphonyl, alkylaminosulphonyl, dialkylaminosulphonyl, alkylcarbonyl, phenylalkylcarbonyl, phenylcarbonyl, carboxy, sulpho, alkoxycarbonyl, aminocarbonylamino, N-aminocarbonyl-alkylamino or aminoalkyl groups, wherein the substituents may be identical or different and the amino group in the above-mentioned aminocarbonylamino, N-aminocarbonyl-alkylamino or aminoalkyl groups may additionally be mono- or disubstituted by alkyl or phenylalkyl groups.

Preferred compounds of general formula I above are, however, those wherein one of the groups $R_a$ or $R_b$ denotes an A—B— group and the other group $R_a$ or $R_b$ denotes an F—E—D— group, wherein A denotes an aminoalkyl group having 1 to 4 carbon atoms in the alkyl moiety, an amino or amidino group, whilst in the above-mentioned amino, aminoalkyl or amidino groups, an amino or imino group may be substituted by an alkyl group or by a group which can be cleaved in vivo, B denotes a phenylene group which may be substituted by a fluorine, chlorine or bromine atom, by an alkyl group, by a trifluoromethyl, hydroxy, alkoxy, alkylsulphenyl, alkylsulphinyl, alkylsulphonyl, $(R_1)_2$N-, N-alkylcarbonyl-$NR_1$- or N-alkanesulphonyl-$NR_1$-, wherein $R_1$ denotes a hydrogen atom or an alkyl or phenylalkyl group, a pyridinylene, pyrimidinylene, pyrazinylene or pyridazinylene group, each of which may be substituted in the carbon skeleton by an alkyl group, a 1,3-pyrrolidinylene, 1,3-piperidinylene, 1,4-piperidinylene, 1,4-piperazinylene or 1,4-homopiperazinylene group, which may be linked via position 1 to the group A or to the cyclic imino group but the link must not be made via a nitrogen-nitrogen bond, and a cycloalkylene group in which a methylene group may be replaced by an —$NR_1$— group wherein $R_1$ is as hereinbefore defined, whilst additionally there must be at least two carbon atoms between the nitrogen atom of the —$NR_1$— group and a nitrogen atom of the group A or of the cyclic imino group, and an indanylidene or 1,2,3,4-tetrahydronaphthylidene group, wherein in each case the aromatic nucleus is linked to the cyclic imino group, or A and B together denote a pyrrolidinyl, piperidinyl or piperazino group optionally substituted in the 1-position by the group $R_1$ or by a group which can be cleaved in vivo, wherein $R_1$ is defined as hereinbefore, D denotes a phenylene group which may be substituted by a fluorine, chlorine or bromine atom, by an alkyl group, by a trifluoromethyl, hydroxy, alkoxy, alkylsulphenyl, alkylsulphinyl, alkylsulphonyl, $(R_1)_2$N-, N-alkylcarbonyl-$NR_1$-, N-alkanesulphonyl-$NR_1$-, carboxymethoxy or alkoxycarbonylmethoxy group, wherein $R_1$ is as hereinbefore defined, a cycloalkylene group, a pyridinylene, pyrimidinylene, pyrazinylene or pyridazinylene group, each of which may be alkyl-substituted in the carbon skeleton, whilst additionally a —CH=N— group may be replaced by a —CO—$NR_2$— group, wherein $R_2$ denotes a hydrogen atom, an alkyl or phenylalkyl group in the alkyl moiety or else denotes a bond with the group E, if there are at least two carbon atoms between a heteroatom of group E or the nitrogen atom of the cyclic imino group to which the group D is linked and the nitrogen atom of the —CONR$_2$— group, a 1,3-pyrrolidinylene, 1,3-piperidinylene, 1,4-piperidinylene, 1,4-piperazinylene or 1,4-homopiperazinylene group, which may be linked via position 1 to the group E or to the cyclic imino group and in which a methylene group adjacent to the nitrogen atom may be replaced by a carbonyl group, but the link may not be made via a nitrogen-nitrogen bond, a cycloalkylene group in which a methylene group is replaced by an —NR$_1$— group, whilst R$_1$ is defined as hereinbefore, E denotes a straight-chained or branched C$_{1-5}$-alkylene group optionally substituted by a hydroxy, alkoxy, amino, alkylamino, dialkylamino, alkyl-CO-NR$_1$-, aryl-CO-NR$_1$-, C$_{1-5}$-alkyl-SO$_2$-NR$_1$- or aryl-SO$_2$-NR$_1$- group, wherein R$_1$ is as hereinbefore defined, a straight-chained or branched C$_{2-5}$-alkenylene group, whilst in a C$_{2-4}$-alkylene group, the methylene group linked to the group D may be replaced by an oxygen or sulphur atom or by a sulphinyl, sulphonyl, imino, alkylimino, phenylalkylimino, alkylcarbonylimino, carboxymethylimino or alkoxycarbonylmethylimino group, and F denotes a group which can be metabolised in vivo to form a carboxyl group, or it denotes a carboxyl group, a sulpho, phosphono, O-alkylphosphono or tetrazol-5-yl group, and either (a) X denotes a methylene or carbonyl group, R$_d$ and R$_e$ together denote another carbon-carbon bond, R$_c$ denotes a hydrogen atom, a C$_{1-5}$-alkyl group, a phenyl group, a hydroxy group, a straight-chained or branched C$_{1-5}$-alkoxy group, whilst a methoxy group may be substituted by a carboxy, alkoxycarbonyl, aminocarbonyl, alkylaminocarbonyl, dialkylaminocarbonyl, piperidinocarbonyl, morpholinocarbonyl, thiomorpholinocarbonyl, 1-oxidothiomorpholinocarbonyl or 1,1-dioxidothiomorpholinocarbonyl group, or R$_c$ denotes a phenylalkoxy, alkylamino, dialkylamino, phenylalkylamino, pyrrolidino or piperidino group, whilst the methylene group may be replaced in the 4-position of a piperidino group by an oxygen or sulphur atom or by a sulphinyl, sulphonyl, imino, alkylimino or alkylcarbonylimino group, R$_f$ denotes a hydrogen atom, a straight-chained or branched alkyl group or a phenyl group and R$_g$ denotes a hydrogen atom or an alkyl group or (b) X denotes a carbonyl group, R$_c$ and R$_e$ together with the carbon atom between them denote a carbonyl group, R$_d$ denotes an alkyl group, a phenylalkyl group or a methyl group optionally substituted by a carboxy, alkoxycarbonyl, aminocarbonyl, alkylaminocarbonyl, dialkylaminocarbonyl, piperidinocarbonyl, morpholinocarbonyl, thiomorpholinocarbonyl, 1-oxidothiomorpholinocarbonyl or 1,1-dioxidothiomorpholinocarbonyl group, R$_f$ denotes a hydrogen atom, an alkyl or phenyl group and R$_g$ denotes a hydrogen atom or a methyl group or (c) X denotes a methylene group, R$_f$ and R$_g$ together with the carbon atom between them denote a carbonyl group, R$_c$ denotes a hydrogen atom or, if B or D denotes a 1,3-pyrrolidinylene, 1,3-piperidinylene, 1,4-piperidinylene, 1,4-piperazinylene or 1,4-homopiperazinylene group which are linked to the cyclic imino group via position 1, but the link must not be made via a nitrogen-nitrogen bond, R$_c$ may also denote a phenyl group and R$_d$ and R$_e$ each represent a hydrogen atom or together denote another carbon-carbon bond or (d) X denotes a methylene or carbonyl group and R$_c$ to R$_f$ each denotes a hydrogen atom, whilst the term "a group which can be metabolised in vivo to form a carboxyl group" and "a group which can be cleaved in vivo" denote for example an ester group of the formulae

—CO—OR',

—CO—O—(HCR")—O—CO—R'" and

—CO—O—(HCR")—O—CO—OR'", wherein

R' denotes a straight-chained or branched C$_{1-6}$-alkyl group, wherein the methyl group may be substituted by a pyridyl, aminocarbonyl, alkylaminocarbonyl, dialkylaminocarbonyl, morpholinocarbonyl, thiomorpholinocarbonyl, 1-oxidothiomorpholinocarbonyl or 1,1-dioxidothiomorpholinocarbonyl group or a C$_{1-3}$-alkyl group may be substituted in the 1-, 2- or 3-position by a phenyl group or in the 2- or 3-position by a morpholino, thiomorpholino, 1-oxidothiomorpholino or 1,1-dioxido-thiomorpholino group, or R' may denote an allyl, cycloalkyl or cinnamyl group, R" denotes a hydrogen atom or an alkyl group and R'" denotes a straight-chained or branched C$_{1-6}$-alkyl group or a cycloalkyl, cycloalkylalkyl or phenylalkyl group, whilst a carboxyl group thus formed after cleaving may, if it is bound to a nitrogen atom of group A, be decarboxylated, thereby releasing the amino or imino group, whilst the alkyl and alkoxy moieties mentioned in the definitions of the above groups may each contain 1 to 3 carbon atoms and the cycloalkyl moieties may each contain 5 or 6 carbon atoms, the stereoisomers thereof, the mixtures thereof and the salts thereof.

However, particularly preferred compounds of general formula I above are those wherein one of the groups R$_a$ or R$_b$ denotes an A—B— group and the other group R$_a$ or R$_b$ denotes an F—E—D— group, wherein A denotes an aminoalkyl group having 1 to 4 carbon atoms in the alkyl moiety, an amino or amidino group, whilst in the above-mentioned amino, aminoalkyl or amidino groups an amino or imino group may be substituted by a methyl group or by a group which can be cleaved in vivo, B denotes a phenylene group which may be substituted by a methyl group or by a fluorine, chlorine or bromine atom, or it may denote a pyridinylene, 1,3-piperidinylene or 1,4-piperidinylene group which may be linked via position 1 to the group A or to the cyclic imino group, but the link must not be made via a nitrogen-nitrogen bond, a cyclohexylene group, an indanylidene or 1,2,3,4-tetrahydronaphthylidene group, wherein the aromatic nucleus in each case is linked to the cyclic imino group, or A and B together denote a piperidinyl group, D denotes a phenylene group which may be substituted by a fluorine, chlorine or bromine atom or by a carboxymethoxy or methoxycarbonylmethoxy group, a cyclohexylene, pyridinylene, pyrimidinylene, 1,3-piperidinylene or 1,4-piperidinylene group, which may be linked via position 1 to group A or to the cyclic imino group, but the link must not be made via a nitrogen-nitrogen bond, E denotes a straight-chained or branched C$_{1-4}$-alkylene group optionally substituted by a hydroxy, methoxy, amino, acetylamino or methanesulphonylamino group, whilst in an alkylene group having 2 or 3 carbon atoms the methylene group linked to the group D may be replaced by an oxygen or sulphur atom or by a sulphinyl, sulphonyl, imino, methylimino, carboxymethylimino or methoxycarbonylmethylimino group, or E denotes an alkenylene group having 2 or 3 carbon atoms and F denotes a group which can be metabolised in vivo to form a carboxyl group, or it denotes a carboxyl group or a phosphono, 0-methyl-phosphono or tetrazol-5-yl group, and either (a) X denotes a carbonyl, group, $R_d$ and $R_e$ together denote a further carbon-carbon bond, $R_c$ denotes a hydrogen atom, a phenyl group, a hydroxy group, a straight-chained or branched $C_{1-3}$-alkoxy group, a phenylmethoxy, morpholinocarbonylmethoxy, methylamino, dimethylamino, phenylamino, pyrrolidino or piperidino group, wherein the methylene group in the 4-position of a piperidino group may be replaced by an oxygen or sulphur atom or by a sulphinyl, sulphonyl, imino or acetylimino group, $R_f$ denotes a hydrogen atom, a methyl group or a phenyl group and $R_g$ denotes a hydrogen atom or a methyl group or (b) X denotes a carbonyl group, $R_c$ and $R_e$ together with the carbon atom between them denote a carbonyl group, $R_d$ denotes a methyl, phenylmethyl or morpholinocarbonylmethyl group, $R_f$ and $R_g$ each denote a hydrogen atom or (c) X denotes a methylene group, $R_f$ and $R_g$ together with the carbon atom between them denote a carbonyl group, $R_c$, $R_d$ and $R_e$ each denote a hydrogen atom or $R_c$ denotes a hydrogen atom or, if B or D denotes a 1,3-piperidinylene or 1,4-piperidinylene group linked to the cyclic imino group via position 1, $R_c$ may denote a phenyl group and $R_d$ and $R_e$ together denote another carbon-carbon bond or (d) X denotes a methylene or carbonyl group and $R_c$ to $R_f$ each denote a hydrogen atom, whilst the terms "a group which can be metabolised in vivo to form a carboxyl group" and "a group which can be cleaved in vivo" denote, for example, an ester group of the formulae

—CO—OR',

—CO—O—(HCR")—O—CO—R''' and

—CO—O—(HCR")—O—CO—OR''', wherein

R' denotes a straight-chained or branched $C_{1-3}$-alkyl group, whilst the methyl group may be substituted by a dimethylaminocarbonyl, piperidinocarbonyl or morpholinocarbonyl group, or R' denotes an allyl, phenylmethyl, 2-morpholinoethyl or cyclohexyl group, R" denotes a hydrogen atom or a methyl group and R''' denotes a straight-chained or branched $C_{1-4}$-alkyl group or a cyclohexyl group, whilst a carboxyl group thus formed after cleaving may, if it is bound to a nitrogen atom of the group A, be decarboxylated thereby releasing the amino or imino group, the stereoisomers, the mixtures thereof and the salts thereof.

Particularly preferred compounds of general formula I, however, are those wherein one of the groups $R_a$ or $R_b$ denotes an A—B— group and the other group $R_a$ or $R_b$ denotes an F—E—D— group, wherein A denotes an aminoalkyl group having 1 to 4 carbon atoms in the alkyl moiety, an amino or amidino group, whilst in the above-mentioned amino, aminoalkyl or amidino groups an amino or imino group may be substituted by a methyl group or by a group which can be cleaved in vivo, B denotes a phenylene group which may be substituted by a methyl group or by a fluorine, chlorine or bromine atom, or B denotes a pyridinylene, 1,3-piperidinylene or 1,4-piperidinylene group which may be linked to the group A or to the cyclic imino group via position 1 but the link must not be made via a nitrogen-nitrogen bond, a cyclohexylene group, an indanylidene or 1,2,3,4-tetrahydronaphthylidene group, wherein in each case the aromatic nucleus is linked to the cyclic imino group, or A and B together denote a piperidinyl group, D denotes a phenylene group which may be substituted by a fluorine, chlorine or bromine atom or by a carboxymethoxy or methoxycarbonylmethoxy group, a cyclohexylene, pyridinylene, pyrimidinylene, 1,3-piperidinylene or 1,4-piperidinylene group which may be linked to the group A or to the cyclic imino group via position 1, but the link must not be made via a nitrogen-nitrogen bond, E denotes a straight-chained or branched $C_{1-4}$-alkylene group optionally substituted by a hydroxy, methoxy or amino group, whilst in a $C_{2-3}$-alkylene group the methylene group linked to the group D may be replaced by an oxygen or sulphur atom or by a sulphinyl, sulphonyl, imino, methylimino, carboxymethylimino or methoxycarbonylmethylimino group, or E denotes a $C_{2-3}$-alkenylene group and F denotes a group which can be metabolised in vivo to form a carboxyl group, or it denotes a carboxyl group, a phosphono, 0-methyl-phosphono or tetrazol- 5-yl group, and either (a) X denotes a carbonyl group, $R_d$ and $R_e$ together denote another carbon-carbon bond, $R_c$ denotes a hydrogen atom, a phenyl group, a hydroxy group, a straight-chained or branched $C_{1-3}$-alkoxy group, a phenylmethoxy, morpholinocarbonylmethoxy, methylamino, dimethylamino, phenylamino, pyrrolidino or piperidino group, whilst the methylene group in the 4-position of a piperidino group may be replaced by an oxygen or sulphur atom or by a sulfinyl, sulphonyl, imino or acetylimino group, $R_f$ denotes a hydrogen atom, a methyl group or a phenyl group and $R_g$ denotes a hydrogen atom or a methyl group or (b) X denotes a carbonyl group, $R_c$ and $R_e$ together with the carbon atom between them denote a carbonyl group, $R_d$ denotes a methyl, phenylmethyl or morpholinocarbonylmethyl group, $R_f$ and $R_g$ each denote a hydrogen atom or (d) X denotes a carbonyl group and $R_c$ to $R_f$ each denote a hydrogen atom, whilst the phrase "a group which can be metabolised in vivo to form a carboxyl group" and "a group which can be cleaved in vivo" refers for example to an ester group of the formulae

—CO—OR',

—CO—O—(HCR")—O—CO—R''' and

—CO—O—(HCR")—O—CO—OR''', wherein

R' denotes a straight-chained or branched $C_{1-3}$-alkyl group, whilst the methyl group may be substituted by a dimethylaminocarbonyl, piperidinocarbonyl or morpholinocarbonyl group, or R' denotes an allyl, phenylmethyl, 2-morpholinoethyl or cyclohexyl group, R" denotes a hydrogen atom or a methyl group and R''' denotes a straight-chained or branched $C_{1-4}$-alkyl group or a cyclohexyl group, whilst a carboxyl group thus formed after cleaving may, if it is bound to a nitrogen atom of the group A, be decarboxylated thereby releasing the amino or imino group, particularly those compounds of the above general formula I wherein one of the groups $R_a$ or $R_b$ denotes an A—B— group and the other group $R_a$ or $R_b$ denotes an F—E—D— group, wherein A denotes an aminomethyl or amidino group,
B denotes a phenylene group,
D denotes a phenylene group,
E denotes an ethylene group and
F denotes a group which can be metabolised in vivo into a carboxyl group or it denotes a carboxyl group, and either (a) X denotes a carbonyl group,
$R_d$ and $R_e$ together denote another carbon-carbon bond,
$R_c$ denotes a hydroxy, methoxy, ethoxy or morpholino group,
$R_f$ and $R_g$ each denote a hydrogen atom or (b) X denotes a carbonyl group,
$R_c$ and $R_e$ together with the carbon atom between them denote a carbonyl group,
$R_d$ denotes a methyl group,
$R_f$ and $R_g$ each denote a hydrogen atom or (d) X denotes a carbonyl group and
$R_c$ to $R_f$ each denote a hydrogen atom, whilst the term "a group which can be metabolised in vivo to form a carboxyl group" denotes an R'O—CO— group in which R' is a straight-chained or branched $C_{1-3}$-alkyl group, the stereoisomers thereof, mixtures thereof and the salts thereof.

The following are examples of particularly preferred compounds:

(a)  1-(4-amidinophenyl)-3-[4-(2-carboxy-ethyl)-phenyl]-4-methoxy-3-pyrrolin-2-one
(b)  1-(4-amidinophenyl)-3-[4-(2-carboxy-ethyl)-phenyl]-4-morpholino-3-pyrrolin-2-one,
(c)  1-(4-amidinophenyl)-3-[4-(2-carboxy-ethyl)-phenyl]-pyrrolidin- 2-one,
(d)  1-(4-aminomethyl-phenyl)-3-[4-(2-carboxy-ethyl)phenyl]- 4-methoxy-3-pyrrolin-2-one and
(e)  1-(4-amidinophenyl)-3-[4-(2-carboxy-ethyl)-phenyl]-3-methyl-pyrrolidin-2,4-dione, the stereoisomers thereof, mixtures thereof and the salts thereof.

The new compounds may, for example, be prepared using the following methods:

a) In order to prepare compounds of general formula I wherein F denotes a carboxyl group:

Conversion of a compound of general formula

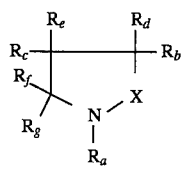

(II)

wherein

X and $R_a$ to $R_g$ are as hereinbefore defined, with the proviso that one of the groups $R_a$ or $R_b$ denotes an A—B— group and the other group $R_a$ or $R_b$ denotes an F'—E—D— group, wherein B, E and D are as hereinbefore defined and F' denotes a group which can be converted into a carboxyl group by hydrolysis, treatment with acids, thermolysis or hydrogenolysis, into a compound of general formula I wherein F denotes a carboxyl group.

For example, functional derivatives of the carboxyl group such as unsubstituted or substituted amides, esters, thioesters, trimethylsilylesters, orthoesters, iminoesters, amidines or anhydrides, or a nitrile group may be converted by hydrolysis into a carboxyl group, esters with tertiary alcohols, e.g. tert.butylesters, may be converted by treatment with an acid or thermolysis into a carboxyl group, and esters with aralkanols, e.g. benzylesters, may be converted by hydrogenolysis into a carboxyl group.

The hydrolysis is appropriately carried out either in the presence of an acid such as hydrochloric acid, sulphuric acid, phosphoric acid, trichloroacetic acid or trifluoroacetic acid, in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane at temperatures between —10° C. and 120° C., e.g. at temperatures between ambient temperature and the boiling temperature of the reaction mixture. When treating with an organic acid such as trichloroacetic acid or trifluoroacetic acid, any alcoholic hydroxy groups present may simultaneously be converted into a corresponding acyloxy group such as a trifluoroacetoxy group.

If F' in a compound of formula II represents a cyano or aminocarbonyl group, these groups may also be converted into a carboxyl group with a nitrite, e.g. sodium nitrite, in the presence of an acid such as sulphuric acid, which may appropriately be used as the solvent at the same time, at temperatures between 0° and 50° C.

If F' in a compound of formula II represents, for example, a tert.butyloxycarbonyl group, the tert.butyl group may also be cleaved by treating with an acid such as trifluoroacetic acid, formic acid, p-toluenesulphonic acid, sulphuric acid, phosphoric acid or polyphosphoric acid, optionally in an inert solvent such as methylene chloride, chloroform, benzene, toluene, tetrahydrofuran or dioxane, preferably at temperatures between –10° C. and 120° C. e.g. at temperatures between 0° and 60° C., or thermally, optionally in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid, preferably at the boiling temperature of the solvent used, e.g. at temperatures between 40° C. and 100° C.

If F' in a compound of formula II represents, for example, a benzyloxycarbonyl group, the benzyl group may also be hydrogenolytically cleaved in the presence of a hydrogenation catalyst such as palladium/charcoal in a suitable solvent such as methanol, ethanol, ethanol/water, glacial acetic acid, ethyl acetate, dioxane or dimethylformamide, preferably at temperatures between 0° and 50° C., e.g. at ambient temperature, under a hydrogen pressure of 1 to 5 bar. During hydrogenolysis, other groups may also be reduced at the same time, e.g. a nitro group may be reduced to an amino group or a benzyloxy group to a hydroxy group, a methoxy group may be reduced by β-elimination to a hydrogen atom or an unsaturated compound may be reduced to a saturated compound.

b) In order to prepare compounds of general formula I wherein A denotes an $H_2N$—C(=NH) group optionally substituted at the amino group by one or two alkyl groups:

Reacting a compound of general formula

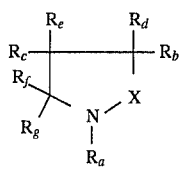   (III)

optionally formed in the reaction mixture, wherein X and $R_a$ to $R_g$ are as hereinbefore defined, with the proviso that one of the groups $R_a$ or $R_b$ denotes an NC—B— group and the other group $R_a$ or $R_b$ denotes an F—E—D— group, wherein B, E and D are as hereinbefore defined, with an amine of general formula $(R_1')_2NH$   (IV)

wherein the groups $R_1'$, which may be identical or different, denote hydrogen atoms or $C_{1-4}$-alkyl groups, or with the acid addition salts thereof.

The reaction is expediently carried out in a solvent such as methanol, ethanol, n-propanol, water, methanol/water, tetrahydrofuran or dioxane at temperatures between 0° and 150° C., preferably at temperatures between 20° and 120° C., with a corresponding free amine or with a corresponding acid addition salt such as for example the corresponding ammonium carbonates, acetates or chlorides.

A compound of general formula III may be obtained, for example, by reacting a corresponding nitrile with a suitable alcohol such as methanol, ethanol, n-propanol, isopropanol or benzyl alcohol in the presence of an acid such as hydrochloric acid or by reacting a corresponding amide with a trialkyloxonium salt such as triethyloxonium-tetrafluoroborate in a solvent such as methylene chloride, tetrahydrofuran or dioxane at temperatures between 0° and 50° C., but preferably at 20° C., or a corresponding nitrile with hydrogen sulphide, appropriately in a solvent such as pyridine or dimethylformamide and in the presence of a base such as triethylamine with subsequent alkylation of the resulting thioamide with a corresponding alkyl or aralkyl halide, or by reacting a corresponding nitrile with an alkoxide such as sodium methoxide in a solvent such as dioxane or tetrahydrofuran, but preferably in the appropriate alcohol.

c) In order to prepare compounds of general formula I wherein at least one of the groups $R_a$ to $R_g$ contains a sulphinyl or sulphonyl group:

Oxidising a compound of general formula

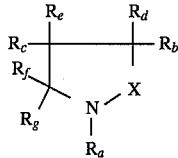   (V)

wherein

X and $R_a$ to $R_g$ are as hereinbefore defined with the proviso that at least one of the groups $R_a$ to $R_g$ contains a sulphenyl or sulphinyl group.

The oxidation is preferably carried out in a solvent or mixture of solvents, e.g. in water, water/pyridine, acetone, methylene chloride, glacial acetic acid, glacial acetic acid/ acetic anhydride, dilute sulphuric acid or trifluoroacetic acid, at temperatures between −80° and 100° C., depending on the oxidising agent used.

In order to prepare a corresponding S-oxide compound of general formula I, oxidation is appropriately carried out with one equivalent of the oxidising agent used, e.g. with hydrogen peroxide in glacial acetic acid, trifluoroacetic acid or formic acid at 0° to 20° C. or in acetone at 0° to 60° C., with a peracid such as performic acid in glacial acetic acid or trifluoroacetic acid at 0° to 50° C. or with m-chloroperbenzoic acid in methylene chloride or chloroform at −20° to 60° C., with sodium metaperiodate in aqueous methanol or ethanol at +15° to 25° C., with bromine in glacial acetic acid or aqueous acetic acid, optionally in the presence of a weak base such as sodium acetate, with N-bromo-succinimide in ethanol, with tert.butyl-hypochlorite in methanol at −80° to −30° C., with iodobenzodichloride in aqueous pyridine at 0° to 50° C., with nitric acid in glacial acetic acid at 0° to 20° C., with chromic acid in glacial acetic acid or in acetone at 0° to 20° C. and with sulphurylchloride in methylene chloride at −70° C. and the resulting thioetherchlorine complex is conveniently hydrolysed with aqueous ethanol.

In order to prepare an S,S-dioxide compound of general formula I, oxidation is expediently carried out, starting from a corresponding alkylsulphinyl compound, conveniently with one or more equivalents of the oxidising agent used, or starting from a corresponding alkylsulphenyl compound with two or more equivalents of the oxidising agent used, e.g. with hydrogen peroxide in glacial acetic acid/acetic anhydride, trifluoroacetic acid or in formic acid at 20° to 100° C. or in acetone at 0° to 60° C., with a peracid such as performic acid or m-chloroperbenzoic acid in glacial acetic acid, trifluoroacetic acid, methylene chloride or chloroform at temperatures between 0° and 60° C., with nitric acid in glacial acetic acid at 0° to 20° C., with chromic acid or potassium permanganate in glacial acetic acid, water/sulphuric acid or in acetone at 0° to 20° C.

d) In order to prepare compounds of general formula I wherein A denotes an amino group, an aminoalkyl group having 1 to 4 carbon atoms in the alkyl moiety, an amidino or guanidino group, whilst in the above-mentioned groups the amino or imino group may be substituted by a $C_{1-4}$-alkyl group or by a phenylalkyl group, all of which are additionally substituted at the nitrogen atom by a group which can be cleaved in vivo:

Reacting a compound of general formula

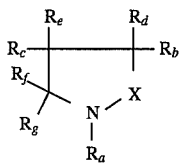   (VI)

wherein

X and $R_a$ to $R_g$ are as hereinbefore defined, with the proviso that one of the groups $R_a$ or $R_b$ denotes an A'—B— group and the other group $R_a$ or $R_b$ denotes an F—E—D— group, wherein B, D, E and F are as hereinbefore defined and A' denotes an amino group, an aminoalkyl group having 1 to 4 carbon atoms in the alkyl moiety, an amidino or guanidino group, whilst in the above-mentioned groups the amino or imino group may be substituted by a $C_{1-4}$-alkyl group or by a phenylalkyl group, with a compound of general formula $Z_1$–$R_3$   (VII)

wherein $R_3$ denotes a group of the formulae

—CO—OR',

—CO—O—(HCR″)—O—CO—R‴ and

—CO—O—(HCR″)—O—CO—OR‴, wherein

R', R″ and R‴ are as hereinbefore defined, and $Z_1$ denotes a nucleophilic leaving group such as a halogen atom, e.g. a chlorine or bromine atom, or an optionally substituted phenoxy group, e.g. a p-nitrophenyloxy group.

The reaction is conveniently carried out in a solvent such as tetrahydrofuran, methylene chloride, chloroform or dimethylformamide, expediently in the presence of a base such as sodium carbonate, potassium carbonate or sodium hydroxide solution or in the presence of a tertiary organic base such as triethylamine, N-ethyldiisopropylamine, N-methyl-morpholine or pyridine, which may simultaneously serve as solvent, at temperatures between −30° and 100° C., but preferably at temperatures between −10° and 80° C.

e) In order to prepare compounds of general formula I wherein A denotes an aminoalkyl group:

Reducing a compound of general formula

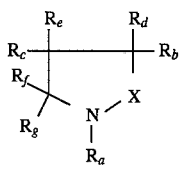
(VIII)

wherein

X and $R_a$ to $R_g$ are as hereinbefore defined, with the proviso that one of the groups $R_a$ or $R_b$ denotes an A"—B— group and the other group $R_a$ or $R_b$ denotes an F—E—D— group, wherein B, D, E and F are as hereinbefore defined and A" denotes a cyano or cyanoalkyl group.

The reduction is preferably carried out in a suitable solvent such as methanol, methanol/water, methanol/water/ammonia, methanol/ammonia, methanol/hydrochloric acid, glacial acetic acid, ethanol, ether, tetrahydrofuran, dioxane or dimethylformamide, in the presence of catalytically activated hydrogen, e.g. hydrogen in the presence of Raney nickel, platinum or palladium/charcoal or in the presence of a metal hydride such as sodium borohydride, lithium borohydride or lithium aluminium hydride at temperatures between 0° and 100° C., preferably at temperatures between 20° and 80° C. During the reduction, other groups may be reduced at the same time, e.g. a nitro group to an amino group, a benzyloxy group to a hydroxy group, a methoxy group to a hydrogen atom by β-elimination or an unsaturated compound to a saturated compound.

f) In order to prepare compounds of general formula I wherein A denotes an amidino group and B denotes a C4-6-cycloalkyleneimino group in which the amidino group is linked to the nitrogen atom of the cycloalkyleneimino group:

Reacting a compound of general formula

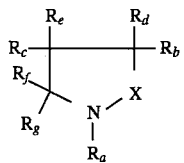
(IX)

wherein

X and $R_a$ to $R_g$ are as hereinbefore defined with the proviso that one of the groups $R_a$ or $R_b$ denotes an H—B"— group and the other group $R_a$ or $R_b$ denotes an F—E—D— group, wherein D, E and F are as hereinbefore defined and B" denotes a $C_{4-6}$-cycloalkyleneimino group, with an S-alkyl-isothiourea in which the alkyl moiety may conveniently contain 1 to 3 carbon atoms.

The reaction is conveniently carried out in a solvent such as dimethylformamide and preferably in the presence of a base such as sodium carbonate at elevated temperatures, e.g. at temperatures between 80° and 120° C.

g) In order to prepare compounds of general formula I wherein $R_e$ and $R_d$ each denote a hydrogen atom:

Hydrogenating a compound of general formula

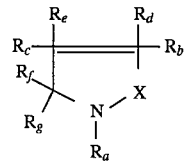
(X)

wherein

X, $R_a$ to $R_c$, $R_f$ and $R_g$ are as hereinbefore defined.

The hydrogenation is preferably carried out in a suitable solvent such as methanol, methanol/water, methanol/water/ammonia, methanol/ammonia, methanol/hydrochloric acid, glacial acetic acid, ethanol, ether, tetrahydrofuran, dioxane or dimethylformamide in the presence of catalytically activated hydrogen, e.g. hydrogen in the presence of Raney nickel, platinum or palladium/charcoal, at temperatures between 0° and 100° C., preferably at temperatures between 20° and 80° C. During hydrogenation, other groups may be reduced at the same time, e.g. a nitro group to an amino group, a benzyloxy group to a hydroxy group, a methoxy group to a hydrogen atom via β-elimination, or an unsaturated compound to a saturated compound.

h) In order to prepare compounds of general formula I wherein F denotes an R'—O—CO—, R'"—CO—O—(HCR")—O—CO— or R'"—O—CO—O—(HCR")—O—CO— group:

Esterifying a compound of general formula

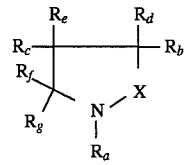
(XI)

wherein X and $R_a$ to $R_g$ are as hereinbefore defined with the proviso that F denotes a carboxy group, or the reactive derivatives thereof, with a compound of general formula $$Z_2\text{-}R_4 \quad (XII)$$

wherein $R_4$ denotes an R'—, R'"—CO—O—(HCR")— or R'"—O—CO—O—(HCR") group, wherein R', R" and R'" are as hereinbefore defined, and $Z_2$ denotes a hydroxy group or a nucleophilic leaving group such as a halogen atom, e.g. a chlorine, bromine or iodine atom.

The esterification is conveniently carried out in a suitable solvent, e.g. in a corresponding alcohol such as methanol, ethanol or isopropanol, methylene chloride, tetrahydrofuran, dioxane, pyridine, toluene or dimethylsulphoxide, in the presence of an acid-activating and/or dehydrating agent such as hydrogen chloride, conc. sulphuric acid, thionylchloride, ethylchloroformate, carbonyldiimidazole or N,N'-dicyclohexyl-carbodiimide or the isourea esters thereof, optionally in the presence of a reaction accelerator such as copper chloride, or by transesterification, e.g. with a corresponding carbonic acid diester.

The reaction with a corresponding halide, preferably with a halide in which $R_4$ denotes an R'"—CO—O—(HCR")— or R'"—O—CO—O—(HCR")— group is preferably carried out in the presence of a base such as triethylamine and optionally in the presence of a reaction accelerator such as potassium iodide at temperatures between 0° and 100° C., but preferably at temperatures between 20° C. and the boiling temperature of the solvent in question.

In the reactions described hereinbefore, any reactive groups present such as hydroxy, carboxy, amino, alkylamino or imino groups may be protected during the reaction by means of conventional protecting groups which are cleaved again after the reaction.

For example, the protective group for a hydroxy group may be a trimethylsilyl, acetyl, benzoyl, tert.butyl, trityl, benzyl or tetrahydropyranyl group, the protecting group for a carboxyl group may be a trimethylsilyl, methyl, ethyl, tert.butyl, benzyl or tetrahydropyranyl group, and the protecting group for an amino, alkylamino or imino group may be an acetyl, benzoyl, ethoxycarbonyl, tert.-butoxycarbonyl, benzyloxycarbonyl, allyloxycarbonyl, benzyl, methoxybenzyl or 2,4-dimethoxybenzyl group and for the amino group a phthalyl group may also be considered.

The optional subsequent cleaving of a protecting group may, for example, be carried out hydrolytically in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or by ether cleaving, e.g. in the presence of iodotrimethylsilane, at temperatures between 0° and 100° C., preferably at temperatures between 10° and 50° C.

However, a benzyl, methoxybenzyl or benzyloxy-carbonyl group may for example be cleaved hydrogenolytically, eg. using hydrogen in the presence of a catalyst such as palladium/charcoal in a solvent such as methanol, ethanol, ethyl acetate or glacial acetic acid, optionally with the addition of an acid such as hydrochloric acid at temperatures between 0° and 50° C., but preferably at ambient temperature, under a hydrogen pressure of 1 to 7 bar, preferably 3 to 5 bar.

A methoxybenzyl group may also be cleaved in the presence of an oxidising agent such as cerium(IV)-ammonium nitrate in a solvent such as methylene chloride, acetonitrile or acetonitrile/water at temperatures between 0° and 50° C., but preferably at ambient temperature.

A 2,4-dimethoxybenzyl group, however, is preferably cleaved in trifluoroacetic acid in the presence of anisol.

A tert.butyl or tert.butyloxycarbonyl group is preferably cleaved by treating with an acid such as trifluoroacetic acid or hydrochloric acid, optionally using a solvent such as methylene chloride, dioxane, or ether.

An allyloxycarbonyl group is cleaved by treating with a catalytic amount of tetrakis-(triphenylphosphine)palladium(O), preferably in a solvent such as tetrahydrofuran and preferably in the presence of an excess of a base such as morpholine or 1,3-dimedone, at temperatures between 0° and 100° C., preferably at ambient temperature and under inert gas, or by treating with a catalytic amount of tris-(triphenylphosphine)rhodium(I)chloride in a solvent such as aqueous ethanol and optionally in the presence of a base such as 1,4diazabicyclo[ 2.2.2]octane at temperatures between 20° and 70° C.

The cleaving of a phthalyl group is preferably carried out in the presence of hydrazine or a primary amine such as methylamine, ethylamine or n-butylamine in a solvent such as methanol, ethanol, isopropanol, toluene/water or dioxane at temperatures between 20° and 50° C.

Furthermore, the compounds of general formula I obtained may be resolved into their enantiomers and/or diastereomers as mentioned hereinbefore. Thus, for example, cis/trans mixtures may be resolved into their cis and trans isomers, and compounds having at least one stereogenic centre may be resolved into their enantiomers.

Thus, for example, the cis/trans mixtures obtained may be resolved by chromatography into the cis and trans isomers thereof and the compounds of general formula I which occur in racemate form may be separated by methods known per se (cf. Allinger N. L. and Eliel E. L. in "Topics in Stereochemistry", Vol. 6, Wiley Interscience, 1971) into their optical antipodes and compounds of general formula I having at least 2 stereogenic centres may be separated on the basis of their physical-chemical differences using known methods, e.g. by chromatography and/or fractional crystallisation, into the diastereomers thereof which, if they occur in racemic form, may subsequently be separated into the enantiomers as mentioned above.

The separation of enantiomers is preferably effected by column separation on chiral phases or by recrystallisation from an optically active solvent or by reacting with an optically active substance which forms salts or derivatives such as esters or amides with the racemic compound, especially acids and the activated derivatives or alcohols thereof, and separation of the diastereomeric salt mixture or derivative thus obtained, e.g. on the basis of their different solubilities, whilst the free antipodes may be released from the pure diastereomeric salts by the action of suitable agents. Particularly common, optically active acids include, for example, the D- and L-forms of tartaric acid and dibenzoyltartaric acid, di-o-tolyl tartaric acid, malic acid, mandelic acid, camphorsulphonic acid, glutamic acid, aspartic acid or quinic acid. Examples of optically active alcohols include for example (+)- or (–)-menthol and examples of optically active acyl groups in amides include for example (+)- or (–)-menthyloxycarbonyl.

Moreover, the compounds of formula I obtained may be converted into the salts thereof, particularly for pharmaceutical use into the physiologically acceptable salts thereof with inorganic or organic acids. Examples of suitable acids include hydrochloric acid, hydrobromic acid, sulphuric acid, phosphoric acid, acetic acid, fumaric acid, succinic acid, lactic acid, citric acid, tartaric acid or maleic acid.

In addition, the new compounds of formula I thus obtained, if they contain a carboxyl group, may subsequently, if desired, be converted into the addition salts thereof with inorganic or organic bases, more particularly, for pharmaceutical use, into the physiologically acceptable addition salts thereof. Examples of suitable bases include sodium hydroxide, potassium hydroxide, ammonia, cyclohexylamine, ethanolamine, diethanolamine and triethanolamine.

The compounds used as starting materials are known from the literature in some cases or may be obtained by methods known from the literature, as described for example in Examples I to VII. Thus, the compounds of general formulae II, III, V, VI and VIII to XI used as starting materials are obtained by cyclisation of a correspondingly substituted arylacetic acid amide which is substituted at the acid amide nitrogen atom by a corresponding β-keto group. A correspondingly, substituted 4-hydroxy-3-pyrrolidin-2-one thus obtained can then be converted into the desired compound by alkylation or by reacting with a corresponding amine. The acetic acid amide required for this is obtained, for example, by reacting a corresponding arylacetic acid amide with a corresponding α-halogenoacetic acid derivative.

As already mentioned, the new 5-membered heterocycles of general formula I and the salts thereof, particularly the physiologically acceptable addition salts thereof with inorganic or organic acids or bases, have valuable properties. Thus, the new compounds, in addition to having an inhibitory effect on inflammation and bone degradation, have in particular antithrombotic, antiaggregatory and tumour- or metastasis-inhibiting effects.

By way of example, the compounds of general formula I were investigated for their biological effects as follows:

1. Inhibition of binding of $^3$H-BIBU 52 to human thrombocytes:

A suspension of human thrombocytes in plasma is incubated with $^3$H-BIBU 52 [= (3S,5S)-5-[(4'-amidino- 4biphenylyl)oxymethyl]-3-[(carboxyl)methyl]-2pyrrolidinone[3-$^3$H-4-biphenylyl]], which replaces the ligand $^{125}$I-fibrinogen known from the literature (see German Patent Application P 42 14 245.8 of the same applicant dated 30.04.1992, internal reference: Case 5/1093-FL) and various concentrations of the substance to be tested. The free and bound ligand is separated by centrifuging and quantitatively determined by scintillation counting. The inhibition of $^3$H-BIBU 52 binding by the test substance is determined from the measurements obtained.

In order to do this, donor blood is taken from an anticubital vein and anticoagulated with trisodium citrate (final concentration 13 mM). The blood is centrifuged for 10 minutes at 170 x g and the supernatant platelet-rich plasma (PRP) is removed. The remaining blood is sharply centrifuged once more in order to obtain plasma. The PRP is diluted 1:10 with autologous plasma. 750 µl are incubated with 50 µl of physiological saline solution, 100 µl of test substance solution, 50 µl of $^{14}$C-sucrose (3,700 Bq) and 50 µl of $^3$H-BIBU 52 (final concentration: 5 nM) at ambient temperature for 20 minutes. In order to measure the non-specific binding, 5 µl of BIBU 52 (final concentration: 30 µM) are used instead of the test substance. The samples are centrifuged for 20 seconds at 10,000 x g and the supernatant is poured off. 100 µl thereof are measured in order to determine the free ligand. The pellet is dissolved in 500 µl of 0.2N NaOH, 450 µl are mixed with 2 ml of scintillator and 25 µl of 5N HCl and measured. The residual plasma remaining in the pellet is determined from the $^{14}$C-content and the bound ligand is determined from the $^3$H-measurement. After the non-specific binding has been deducted, the pellet activity is plotted against the concentration of the test substance and the concentration for a 50% inhibition of binding is determined.

2. Antithrombotic activity

Method

The thrombocyte aggregation is measured using the Born and Cross method (J. Physiol. 170:397 (1964)) in platelet-rich plasma taken from healthy volunteers. To inhibit coagulation the blood is mixed with 3.14% sodium citrate in a volume ratio of 1:10.

Collagen-induced aggregation

The pattern of the decrease in optical density of the platelet suspension is photometrically measured and recorded after the addition of the aggregation-triggering substance. The rate of aggregation is determined from the angle of inclination of the density curve. The point on the curve where there is maximum light transmittance is used to calculate the optical density.

The amount of collagen used is as small as possible but sufficient to produce an irreversible reaction curve. Standard commercial collagen produced by Hormonchemie of Munich is used.

Before the addition of the collagen the plasma is incubated for 10 minutes with the substance at 37° C.

From the measurements obtained an $EC_{50}$ is determined graphically, indicating a 50% change in the optical density in terms of the inhibition of aggregation. The Table which follows contains the results found:

| Substance (Example No.) | Fibrinogen-binding test $IC_{50}$ [nM] | Inhibition of platelet aggregation $EC_{50}$ [nM] |
| --- | --- | --- |
| 2 | 11 | 40 |
| 2(3) | 42 | 730 |
| 2(13) | 110 | 260 |
| 2(55) | 180 | 330 |
| 5(B) | 8,600 | 380 |
| 13 | 360 | 500 |

The compounds according to the invention are well tolerated because after intravenous administration of 15 mg/kg of the compound of Example 2 to mice, none of the 3 animals tested died.

In the light of their inhibitory effect on cell-cell or cell-matrix interactions, the new cyclic urea derivatives of general formula I and the physiologically acceptable addition salts thereof are suitable for combating or preventing diseases in which smaller or greater cell aggregates occur or in which cell-matrix interactions play a part, e.g. in treating or preventing venous and arterial thrombosis, cerebrovascular diseases, lung embolism, cardiac infarction, arteriosclerosis, osteoporosis and the metastasis of tumours and the treatment of genetically caused or acquired disorders of cell interactions with one another or with solid structures. They are also suitable for parallel therapy in thrombolysis with fibrinolytics or vascular interventions such as transluminal angioplasty or in the treatment of shock, psoriasis, diabetes and inflammation.

For treating or preventing the diseases mentioned above the dosage is between 0.1 µg and 20 mg/kg of body weight, preferably 1 µg to 10 mg/kg of body weight, given in up to 4 doses per day. For this purpose the compounds of formula I produced according to the invention, optionally in conjunction with other active substances such as thromboxane receptor antagonists and thromboxane synthesis inhibitors or combinations thereof, serotonin antagonists, α-receptor antagonists, alkylnitrates such as glycerol trinitrate, phosphodiesterase inhibitors, prostacyclin and the analogues thereof, fibrinolytics such as tPA, prourokinase, urokinase, streptokinase, or anticoagulants such as heparin, dermatane sulphate, activated protein C, vitamin K antagonists, hirudine, inhibitors of thrombin or other activated clotting factors, may be incorporated together with one or more inert conventional carriers and/or diluents, e.g. corn starch, lactose, sucrose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof, into conventional galenic preparations such as plain or coated tablets, capsules, powders, suspensions, solutions, sprays or suppositories.

The Examples which follow are intended to illustrate the invention:

Preparation of the starting compounds:

EXAMPLE I

Methyl p-(carboxymethyl)-cinnamate

Under inert gas, a solution of 32.3 g of 4-bromophenylacetic acid, 21 g of methyl acrylate, 44 g of triethylamine, 2.5 g of tri-o-tolylphosphine and 0.5 g of palladium(II)acetate is refluxed for 4.5 hours. After cooling, the reaction mixture is stirred into 600 ml of ice-cooled dilute hydrochloric acid. The aqueous phase is extracted three times with ethyl acetate, the organic phase is dried over sodium sulphate and the solvent is distilled off. The solid remaining is triturated with ethyl acetate and suction filtered.

Yield: 28.5 g (86% of theory),

Melting point: 120°–126° C.

$R_f$ value: 0.40 (silica gel; methylene chloride/methanol= 9:1)

EXAMPLE II

Methyl 3-(4-carboxymethyl-phenyl)-propionate 18.0 g of methyl p-(carboxymethyl)-cinnamate in 900 ml of glacial acetic acid are hydrogenated for 2 hours at ambient temperature under a hydrogen pressure of 5 bar in the presence of 2 g of 10% palladium on activated charcoal. The catalyst is then filtered off and the filtrate is evaporated down. The solid obtained is triturated with water and suction filtered.

Yield: 17.5 g (96% of theory),

Melting point: 101°–104° C.

$R_f$ value: 0.12 (silica gel; methylene chloride/methanol= 20:1)

EXAMPLE III

Methyl 3-[4-[[(4-cyanophenyl)-aminocarbonyl]-methyl]phenyl]-propionate

Under inert gas at –20° C. 44.5 g of diphenylphosphinic acid chloride are added dropwise to a solution of 33.0 g of methyl 3-(4-carboxymethylphenyl)-propionate and 15.7 g of triethylamine in 250 ml of anhydrous tetrahydrofuran. The mixture is stirred for 60 minutes at –20° C. and at this temperature a solution of 17.72 g of 4-aminobenzonitrile and 18.3 g of dimethylaminopyridine in 250 ml of anhydrous tetrahydrofuran is added. The resulting mixture is stirred for 30 minutes at –20° C., the cooling bath is removed and the mixture is stirred for a further 16 hours at ambient temperature. The suspension is diluted with 500 ml of ethyl acetate and the solution is washed once with 1N hydrochloric acid and once with water. The organic phase is dried over sodium sulphate, the solvent is evaporated down and the residue remaining is chromatographed with methylene chloride/methanol (20:1) over silica gel.

Yield: 19.5 g (41% of theory),

Melting point: 146°–148° C.

$R_f$ value: 0.18 (silica gel; methylene chloride/methanol= 20:1)

EXAMPLE IV

Methyl 3-[4-[[N-(4-cyanophenyl)-N-[(methoxycarbonyl)methyl]-aminocarbonyl]-methyl]-phenyl]-propionate A solution of 14.5 g of methyl 3-[4-[[( 4-cyanophenyl)aminocarbonyl]-methyl]-phenyl]-propionate in 100 ml of anhydrous dimethylformamide is mixed batchwise, under inert gas and at –40° C., with 1.96 g of a 55% dispersion of sodium hydride in mineral oil. The cooling bath is taken away and the mixture is stirred until the sodium hydride has dissolved completely. Then at –30° C. 23.0 g of methyl bromoacetate are added dropwise and the mixture is stirred for 30 minutes at this temperature. The cooling bath is removed and the mixture is stirred for 16 hours at ambient temperature. The reaction solution is poured onto 500 ml of 1N hydrochloric acid and the aqueous phase is extracted three times with ethyl acetate. The organic phase is washed with water, dried over sodium sulphate and the solvent is evaporated down. The residue is chromatographed over silica gel with methylene chloride/methanol (9:1). 11.0 g of product are obtained which is contaminated with the starting material and is used in Example V without any further purification.

$R_f$ value: 0.71 (silica gel; methylene chloride/methanol= 9:1)

EXAMPLE V

1-(4-Cyanophenyl)-4-hydroxy-3-[4-(2-methoxycarbonyl-ethyl)-phenyl]-3-pyrrolin-2-one 3.4 g of potassium tert.butoxide are added to a solution of 11.0 g of methyl 3-[4-[[N-(4-cyanophenyl)-N[ (methoxycarbonyl)-methyl]-aminocarbonyl]-methyl]phenyl]-propionate (product of Example IV) in 50 ml of tetrahydrofuran/ dimethylformamide (3:2), whilst cooling in an ice/water bath. The mixture is stirred at ambient temperature for 60 minutes, the reaction solution is poured into 1N hydrochloric acid and the aqueous phase is extracted three times with ethyl acetate. The combined organic phases are washed with water, dried over sodium sulphate and the solvent is evaporated off. The crude product is triturated with ethyl acetate, the precipitate is suction filtered and dried.

Yield: 2.6 g (16% of theory based on the last two steps),

Melting point: 245°–250° C. Mass spectrum: $M^+= 362$ $R_f$ value: 0.43 (silica gel; methylene chloride/methanol= 9:1)

EXAMPLE VI

1-(4-Cyanophenyl)-3-[4-(2-methoxycarbonyl-ethyl)phenyl]-4-morpholino-3-pyrrolin-2-one A solution of 0.50 g of 1-(4-cyanophenyl)-4-hydroxy-3-[ 4-(2-methoxycarbonyl-ethyl)-phenyl]-3-pyrrolin-2-one in 10 ml of morpholine, 200 ml of xylene and 60 ml of glacial acetic acid is refluxed for 5 hours using a water separator. Under reduced pressure the solvent is evaporated down at 150° C. and the residue is chromatographed over silica gel using methylene chloride/methanol (20:1).

Yield: 0.36 g (60% of theory),

Melting point: 196°–200° C. Mass spectrum: $M^+=431$ $R_f$ value: 0.74 (silica gel; methylene chloride/methanol= 9:1)

EXAMPLE VII 1-(4-Cyanophenyl)-4-methoxy-3-[4-(2-methoxycarbonyl-ethyl)-phenyl]-3-pyrrolin-2-one and 1-(4-Cyanophenyl)-3-[4-(2-methoxycarbonyl-ethyl)phenyl]-3-methyl-pyrrolidin-2,4-dione To a solution of 1.40 g of 1-(4-cyanophenyl)-4-hydroxy-3-[4-(2-methoxycarbonyl-ethyl)-phenyl]-3-pyrrolin-2-one in 30 ml of absolute dimethylformamide, 0.46 g of potassium tert.butoxide are added at −15° C. The mixture is allowed to come up to 0° C. and 0.3 ml of methyliodide are added dropwise. After 2 hours, 0.35 ml of methyliodide and after 4 hours a further 0.5 ml of methyliodide are added dropwise and the conversion is monitored by thin layer chromatography. After 6 hours the reaction solution is poured onto ice/water and the aqueous phase is extracted with ethyl acetate. The organic phase is washed with water, dried over sodium sulphate and the solvent is evaporated down under reduced pressure. The crude product is chromatographed over silica gel with ethyl acetate/cyclohexane (1:1).

Yield: 660 mg of 1-(4-cyanophenyl)-3-[4-( 2-methoxycarbonyl-ethyl)-phenyl]-3-methyl-pyrrolidin-2,4-dione (45% of theory), Melting point: 108°–111° C.

$R_f$ value: 0.57 (silica gel; ethyl acetate/cyclohexane= 1:1)

Yield: 470 mg of 1-(4-cyanophenyl)-4-methoxy-3-[4-( 2-methoxycarbonyl-ethyl)-phenyl]-3-pyrrolin-2-one (32% of theory), Melting point: 163°–168° C.

$R_f$ value: 0.28 (silica gel; ethyl acetate/cyclohexane= 1:1)

EXAMPLE 1

1-(4-Amidinophenyl)-4-methoxy-3-[4-(2-methoxycarbonyl-ethyl)-phenyl]-3-pyrrolin-2-one-hydrochloride 0.75 g of 1-(4-cyanophenyl)-4-methoxy-3-[4-( 2-methoxycarbonyl-ethyl)-phenyl]-3-pyrrolin-2-one are suspended in 200 ml of absolute methanol. Whilst cooling in an ice/water bath, dry hydrogen chloride is introduced for one hour. The reaction solution is stirred at ambient temperature and the conversion is monitored by thin layer chromatography. After 4 hours the reaction solution is evaporated down under reduced pressure at a bath temperature of 35° C. The residue is dissolved in 150 ml of absolute methanol and the solution is mixed with 5 g of ammonium carbonate with stirring. It is stirred for 16 hours at ambient temperature, the precipitate is removed by suction filtering and washed with water.

Yield: 0.48 g (56% of theory),

Mass spectrum: $(M+H)^+= 394$ $R_f$ value: 0.57 (silica gel; methylene chloride/methanol/conc. ammonia= 2:1:0.25)

The following compounds are obtained analogously:

(1) 1-(4-amidino)-3-[4-(2-methoxycarbonyl-ethyl)phenyl]- 4-morpholino-3-pyrrolin-2-one-hydrochloride Mass spectrum: $M^+= 448$ $R_f$ value: 0.14 (silica gel; methylene chloride/methanol/conc. ammonia= 4:1:0.25)

(2) 1-(4-amidinophenyl)-4-hydroxy-3-[4-( 2-methoxycarbonyl-ethyl)-phenyl]-3-pyrrolin-2-one-hydrochloride Mass spectrum: $(M+H)^+=380$ $R_f$ value: 0.58 (silica gel; methylene chloride/methanol/conc. ammonia= 2:1:0.25)

(3) 1-(4-amidinophenyl)-4-methoxy-3-[4-( 2-methoxycarbonyl-ethenyl)-phenyl]-3-pyrrolin-2-one-hydrochloride (4) 1-(4-amidinophenyl)-3-[4-(2-methoxycarbonyl-ethyl)phenyl]- 4-pyrrolidino-3-pyrrolin-2-one-hydrochloride (5) 1-(4-amidinophenyl)-4-methoxy-3-[4-( 2-methoxycarbonyl-ethyl)-phenyl]-5-methyl-3-pyrrolin-2-one-hydrochloride (6) 1-(4-amidinophenyl)-4-methoxy-3-[ 4-(2-methoxycarbonyl-ethyl)-phenyl]- 5-phenyl-3-pyrrolin-2-one-hydrochloride (7) 1-(4-amidinophenyl)-3-[4-(2-methoxycarbonyl-ethyl)-phenyl]- 4-methylamino-3-pyrrolin-2-one-hydrochloride (8) 1-(4-amidinophenyl)-4-methoxy-3-[4-[ (methoxycarbonyl)-methyloxy]-phenyl]-3-pyrrolin-2-one-hydrochloride (9) 1-(4-amidinophenyl)-4-N,N-dimethylamino-3-[4-(2-methoxy-carbonyl-ethyl)-phenyl]-3-pyrrolin-2-one-hydrochloride

(10) 1-(4-amidinophenyl)-3-[4-[N,N-di-(methoxycarbonyl-methyl)-amino]-phenyl]- 4-methoxy-3-pyrrolin-2-one-hydrochloride

(11) 1-(4-amidinophenyl)-3-[4-(2-methoxycarbonyl-ethyl)phenyl]- 4-(N-phenylamino)-3-pyrrolin-2-one-hydrochloride

(12) 1-(4-amidinophenyl)-3-[4-(2-methoxycarbonyl-ethyl)phenyl]- 3-pyrrolin-2-one-hydrochloride

(13) 1-(4-amidinophenyl)-3-[4-(2-methoxycarbonyl-ethyl)phenyl]- 4-phenyl-3-pyrrolin-2-one-hydrochloride

(14) 1-(4-amidinophenyl)-4-[4-( 2-methoxycarbonyl-ethyl)phenyl]-3-pyrrolin- 2-one-hydrochloride

(15) 1-(4-amidinophenyl)-4-[4-( 2-methoxycarbonyl-ethyl)phenyl]-pyrrolidin- 2-one-hydrochloride

(16) 3-(4-amidinophenyl)-4-methoxy-1-[4-( 2-methoxycarbonyl-ethyl)-phenyl]-3-pyrrolin-2-one-hydrochloride

(17) 1-(4-amidinophenyl)-3-[4-( 2-methoxycarbonyl-ethyl)phenyl]-pyrrolidine-hydrochloride

(18) 1-(5-amidinopyrid-2-yl)-3-[4-( 2-methoxycarbonyl-ethyl)-phenyl]-pyrrolidin-2-one-hydrochloride

(19) 3-(4-amidinophenyl)-4-methoxy-1-[4-( 2-methoxycarbonyl-ethyl)-cyclohexyl]-3-pyrrolin-2-one-hydrochloride

(20) 3-(4-amidinophenyl)-4-isopropoxy-1- [4-( 2-methoxycarbonyl-ethyl)-phenyl]-3-pyrrolin-2-one-hydrochloride

(21) 1-(4-amidino-2-methylphenyl)-4-methoxy-3- [4-(2-methoxycarbonyl-ethyl)-phenyl]-3-pyrrolin-2-one-hydrochloride

(22) 1-(4-amidino-2-fluorophenyl)-4-methoxy-3-[4-(2-methoxycarbonyl-ethyl)-phenyl]-3-pyrrolin-2-one-hydrochloride

(23) 1-(4-amidinophenyl)-4-methoxy-3-[2-( 2-methoxycarbonyl-ethyl)-pyrimid-5-yl]-3-pyrrolin-2-one-hydrochloride

(24) 1-(4-amidinophenyl)-3-[4-(2-methoxycarbonyl-ethyl)phenyl]- 3-(morpholinocarbonyl-methyl)-pyrrolidin-2,4-dione-hydrochloride

(25) 1-(4-amidinophenyl)-5,5-dimethyl-4-methoxy-3-[4-(2-methoxycarbonyl-ethyl)-phenyl]-3-pyrrolin-2-one-hydrochloride

(26) 4-(4-acylpiperazin-1-yl)-1-(4-amidinophenyl)-3-[4-(2-methoxycarbonyl-ethyl)-phenyl]-3-pyrrolin-2-one-hydrochloride

(27) 1-(4-amidinophenyl)-4-benzyloxy-3-[4-( 2-methoxycarbonyl-ethyl)-phenyl]-3-pyrrolin-2-one-hydrochloride

(28) 1-(4-amidinophenyl)-3-[4-(2-methoxycarbonyl-ethyl)phenyl]- 3-methyl-pyrrolidin-2,4-dione-hydrochloride Mass spectrum: $M^+=393$ $R_f$ value: 0.26 (silca gel; methylene chloride/methanol/conc. ammonia= 4:1:0.25)

(29) 1-(4-amidinophenyl)-3-[4-(2-methoxycarbonyl-ethyl)phenyl]- 4-piperidino-3-pyrrolin-2-one-hydrochloride

(30) 3-(4-amidinophenyl)-4-methoxy-1-[4-(2,2-dimethyl-2-methoxycarbonyl-ethyl)-phenyl]-3-pyrrolin-2-one-hydrochloride

(31) 3-(4-amidinophenyl)-4-ethoxy-1-[4-( 2-methoxycarbonyl-ethyl)-phenyl]-3-pyrrolin-2-one-hydrochloride

(32) 1-(4-amidinophenyl)-4-[4-( 2-methoxycarbonyl-ethyl)piperidino]-3-phenyl-3-pyrrolin-2-one-hydrochloride

(33) 1-(4-amidinophenyl)-4-methoxy-3-[3,4-di[ (methoxycarbonyl)-methyloxy]-phenyl]-3-pyrrolin-2-one-hydrochloride

(34) 1-(4-amidinophenyl)-3-[2-chloro-4-( 2-methoxycarbonyl-ethyl)-phenyl]-4-methoxy-3-pyrrolin-2-one-hydrochloride

(35) 1-(4-amidinophenyl)-3-[4-(2-methoxycarbonyl-ethyl)phenyl]- 4-thiomorpholino-3-pyrrolin-2-one-hydrochloride

(36) 1-(4-amidinophenyl)-4-methoxy-3-[4-[ N-(methoxycarbonyl-methyl)-amino]-phenyl]-3-pyrrolin-2-one-hydrochloride

(37) 1-(4-amidinophenyl)-4-methoxy-3-[4-[ N-(methoxycarbonyl-methyl)-methylamino]-phenyl]-3-pyrrolin-2-one-hydrochloride

(38) 3-(4-amidinophenyl)-4-methoxy-1-[1-( 2-methoxycarbonyl-ethyl)-piperid-4-yl]-3-pyrrolin-2-one-hydrochloride

(39) 1-(4-amidinophenyl)-4-methoxy-3-[4-( 3-methoxycarbonyl-propyl)-phenyl]-3-pyrrolin-2-one-hydrochloride

(40) 4-methoxy-3-[4-(2-methoxycarbonyl-ethyl)-phenyl]-1-[ 4-(N-methylamidino)-phenyl]-3-pyrrolin-2-one-hydrochloride The iminoester is dissolved in absolute methanol and reacted with a 20-fold excess of a methanolic methylamine solution.

(41) 1-(4-amidinophenyl)-4-methoxy-3-[ 4-(methoxycarbonyl)-methylsulphonyl]-phenyl]-3-pyrrolin- 2-one-hydrochloride

(42) 1-(4-amidinophenyl)-4-methoxy-3-[ 4-(methoxycarbonyl)-methylsulphenyl]-phenyl]-3-pyrrolin- 2-one-hydrochloride

(43) 1-(4-amidinophenyl)-4-(1,1-dioxido-thiomorpholino)-3-[4-(2-methoxycarbonyl-ethyl)-phenyl]-3-pyrrolin-2-one-hydrochloride

(44) 1-(4-amidinophenyl)-4-methoxy-3-[4-( 2-phosphonoethyl)-phenyl]-3-pyrrolin-2-one-hydrochloride

(45) 1-(4-amidinophenyl)-4-methoxy-3-[4-[2-( 0-methylphosphono)-ethyl]-phenyl]-3-pyrrolin-2-one-hydrochloride

(46) 1-(4-amidinophenyl)-4-methoxy-3-[4-[2-(tetrazol-5-yl)-ethyl]-phenyl]-3-pyrrolin-2-one-hydrochloride

(47) 3-(4-amidinophenyl)-1-[4-[2-amino- 2-(methoxycarbonyl)-ethyl]-phenyl]-4-methoxy-3-pyrrolin-2-one-hydrochloride

(48) 3-(4-amidinophenyl)-1-[4-[2-hydroxy- 2-(methoxycarbonyl)-ethyl]-phenyl]-4-methoxy-3-pyrrolin-2-one-hydrochloride

(49) 1-(4-amidinophenyl)-4-methoxy-3-[3-[ (methoxycarbonyl)-methyloxy]-phenyl]-3-pyrrolin-2-one-hydrochloride

(50) 1-(4-amidinophenyl)-3-benzyl-3-[4-( 2-methoxycarbonyl-ethyl)-phenyl]-pyrrolidin-2,4-dione-hydrochloride

(51) 1-(4-amidinophenyl)-3- [4-(2-methoxycarbonyl-ethyl)phenyl]- 4-(morpholinocarbonyl-methoxy)-3-pyrrolin-2 -one-hydrochloride

(52) 1-[4-[2-(acetylamino)-2-(methoxycarbonyl)-ethyl]phenyl]- 3-(4-amidinophenyl)-4-methoxy-3-pyrrolin-2-one-hydrochloride

(53) 3-(4-amidinophenyl)-4-methoxy-1-[4-[ 2-(methanesulphonyl-amino)-2-(methoxycarbonyl)-ethyl]phenyl]-3-pyrrolin-2-one-hydrochloride

EXAMPLE 2

1-(4-Amidinophenyl)-3-[4-(2-carboxyethyl)-phenyl]-4-methoxy-3-pyrrolin-2one-hydrochloride A solution of 150 mg of 1-(4-amidinophenyl)-4-methoxy-3-[ 4-(2-methoxycarbonyl-ethyl)-phenyl]-3-pyrrolin-2-one and 64 mg of lithium hydroxide-monohydrate in a mixture of 10 ml of tetrahydrofuran and 8 ml of water is stirred for 2 hours at ambient temperature. It is then acidified with 2 ml of 1N hydrochloric acid and the tetrahydrofuran is evaporated off in vacuo. The precipitate is suction filtered and washed with water.

Yield: 130 mg (90% theory), Mass spectrum: $(M+H)^+=$ 380

$R_f$ value: 0.20 (silica gel; methylene chloride/methanol/ conc. ammonia= 2:1:0.25)

(1) 1-(4-amidinophenyl)-3-[4-(2-carboxy-ethenyl)phenyl]-4-methoxy-3-pyrrolin-2-one-hydrochloride (2) 1-(4-amidinophenyl)-3-[4-(2-carboxy-ethyl)-phenyl]-4-hydroxy-3-pyrrolin-2-one-hydrochloride Mass spectrum: $(M+H)^+=366$ $R_f$ value: 0.16 (silica gel; methylene chloride/methanol/ conc. ammonia= 2:1:0.25)

(3) 1-(4-amidinophenyl)-3-[4-(2-carboxy-ethyl)-phenyl]-4-morpholino-3-pyrrolin-2-one-hydrochloride Mass spectrum: $(M+H)^+= 435$ $R_f$ value: 0.43 (silica gel; methylene chloride/methanol/ conc. ammonia= 2:1:0.25)

(4) 1-(4-amidinophenyl)-3-[4-(2-carboxy-ethyl)-phenyl]-4-pyrrolidino-3-pyrrolin-2-one-hydrochloride (5) 1-(4-amidinophenyl)-3-[4-(2-carboxy-ethyl)-phenyl]-4-methoxy-5-methyl-3-pyrrolin-2-one-hydrochloride (6) 1-(4-amidinophenyl)-3-[4-(2-carboxy-ethyl)-phenyl]-4-methoxy-5-phenyl-3-pyrrolin-2-one-hydrochloride (7) 1-(4-amidinophenyl)-3-[ 4-(2-carboxy-ethyl)-phenyl]-4-methylamino-3-pyrrolin-2-one-hydrochloride (8) 1-(4-amidinophenyl)-3-[4-(carboxymethyloxy)-phenyl]-4-methoxy-3-pyrrolin-2-one-hydrochloride (9) 1-(4-amidinophenyl)-3-[4-(2-carboxy-ethyl)-phenyl]-4-dimethylamino-3-pyrrolin-2-one-hydrochloride

(10) 1-(4-amidinophenyl)-3-[4-[ N,N-di-(carboxymethyl)amino]-phenyl]-4-methoxy- 3-pyrrolin-2-one-hydrochloride

(11) 1-(4-amidinophenyl)-3-[4-(2-carboxy-ethyl)-phenyl]-4-(N-phenylamino)-3-pyrrolin-2-one-hydrochloride

(12) 1-(4-amidinophenyl)-3-[4-(2-carboxy-ethyl)-phenyl]-3-pyrrolin-2-one-hydrochloride

(13) 1-(4-amidinophenyl)-3-[4-( 2-carboxy-ethyl)-phenyl]-pyrrolidin-2-one-hydrochloride Mass spectrum: $(M+H)^+=352$ $R_f$ value: 0.20 (silica gel; methylene chloride/methanol/ conc. ammonia= 2:1:0.25)

(14)1-(4-amidinophenyl)-4-[4-(2-carboxy-ethyl)-phenyl]-3-pyrrolin-2-one-hydrochloride

(15) 1-(4-amidinophenyl)-4-[4-( 2-carboxy-ethyl)-phenyl] pyrrolidin-2-one-hydrochloride

(16) 3-(4-amidinophenyl)-1-[4-(2-carboxy-ethyl)-phenyl]-4-methoxy-3-pyrrolin-2-one-hydrochloride

(17) 1-(4-amidinophenyl)-3-[4-( 2-carboxy-ethyl)-phenyl] pyrrolidine-hydrochloride

(18) 1-(5-amidinopyrid-2-yl)-3-[4-( 2-carboxy-ethyl)phenyl]-pyrrolidin-2-one-hydrochloride
(19) 3-(4-amidinophenyl)-1-[4-( 2-carboxy-ethyl)cyclohexyl]-4-methoxy-3-pyrrolin-2-one-hydrochloride
(20) 3-(4-amidinophenyl)-1-[4-(2-carboxy-ethyl)-phenyl]-4-isopropoxy-3-pyrrolin-2-one-hydrochloride
(21) 1-(4-amidinophenyl-2-methylphenyl)-3-[4-( 2-carboxyethyl)-phenyl]-4-methoxy-3-pyrrolin-2-one-hydrochloride
(22) 1-(4-amidino-2-fluorophenyl)-3-[4-( 2-carboxyethyl)-phenyl]-4-methoxy-3-pyrrolin-2-one-hydrochloride
(23) 1-(4-amidinophenyl)-3-[2-(2-carboxy-ethyl)-pyrimid-5-yl]-4-methoxy-3-pyrrolin-2-one-hydrochloride
(24) 1-(4-amidinophenyl)-3-[4-(2-carboxy-ethyl)-phenyl]-4-phenyl-3-pyrrolin-2-one-hydrochloride
(25) 1-(4-amidinophenyl)-3-[4-(2-carboxy-ethyl)-phenyl]-5,5-dimethyl-4-methoxy-3-pyrrolin-2-one-hydrochloride
(26) 4-(4-acetylpiperazin-1-yl)-1-(4-amidinophenyl)-3-[4-(2-carboxy-ethyl)-phenyl]-3-pyrrolin-2-one-hydrochloride
(27) 1-(4-amidinophenyl)-4-benzyloxy-3-[4-( 2-carboxyethyl)-phenyl]-3-pyrrolin-2-one-hydrochloride
(28) 1-(4-amidinophenyl)-3-[ 3-(carboxy-methyloxy)phenyl]-4-methoxy-3-pyrrolin-2-one-hydrochloride
(29) 1-(4-amidinophenyl)-3-[4-(2-carboxy-ethyl)-phenyl]-4-piperidino-3-pyrrolin-2-one-hydrochloride
(30) 3-(4-amidinophenyl)-1-[4-(2-carboxy- 2,2-dimethylethyl)-phenyl]-4-methoxy-3-pyrrolin-2-one-hydrochloride
(31) 3-(4-amidinophenyl)-1-[4-(2-carboxy-ethyl)-phenyl]-4-ethoxy-3-pyrrolin-2-one-hydrochloride
(32) 1-(4-amidinophenyl)-4-[4-(2-carboxy-ethyl)piperidino]- 3-phenyl-3-pyrrolin-2-one-hydrochloride
(33) 1-(4-amidinophenyl)-3-[ 3,4-di-[(carboxymethyl)oxy]-phenyl]-4-methoxy-3-pyrrolin-2-one-hydrochloride
(34) 1-(4-amidinophenyl)-3-[2-chloro-4-( 2-carboxyethyl)phenyl]-4-methoxy-3-pyrrolin-2-one-hydrochloride
(35) 1-(4-amidinophenyl)-3-[4-(2-carboxy-ethyl)-phenyl]-4-thiomorpholino-3-pyrrolin-2-one-hydrochloride
(36) 1-(4-amidinophenyl)-3-[4-(2-carboxy-ethyl)-phenyl]-4-(1-oxido-thiomorpholino)-3-pyrrolin-2-one-hydrochloride
(37) 1-(4-amidinophenyl)-3-[4-(2-carboxy-ethyl)-phenyl]-4-(1,1-dioxido-thiomorpholino)-3-pyrrolin-2-one-hydrochloride
(38) 1-(4-amidinophenyl)-3-[4-(carboxymethyl-sulphenyl)phenyl]- 4-methoxy-3-pyrrolin-2-one-hydrochloride
(39) 1-(4-amidinophenyl)-3-[4-(carboxymethyl-sulphinyl)phenyl]- 4-methoxy-3-pyrrolin-2-one-hydrochloride
(40) 1-(4-amidinophenyl)-3-[4-(carboxymethyl-sulphonyl)phenyl]- 4-methoxy-3-pyrrolin-2-one-hydrochloride
(41) 1-(4-amidinophenyl)-3-[4-(carboxymethyl-amino)phenyl]- 4-methoxy-3-pyrrolin-2-one-hydrochloride
(42) 1-(4-amidinophenyl)-3-[ 4-(N-carboxymethyl-methylamino)-phenyl]-4-methoxy-3-pyrrolin-2-one-hydrochloride
(43) 3-(4-amidinophenyl)-1-[1-(2-carboxy-ethyl)-piperid-4-yl]-4-methoxy-3-pyrrolin-2-one-hydrochloride
(44) 1-(4-amidinophenyl)-3-[4-(3-carboxy-propyl)phenyl]-4-methoxy-3-pyrrolin-2-one-hydrochloride
(45) 3-[4-(2-carboxy-ethyl)-phenyl]-4-methoxy-1-[ 4-(N-methyl-amidino)-phenyl-3-pyrrolin-2-one-hydrochloride
(46) 1-(1-amidinopiperid-4-yl)-3-[4-(2-carboxy-ethyl)phenyl]- 4-methoxy-3-pyrrolin-2-one-hydrochloride
(47) 3-(4-amidinophenyl)-1-[4-(2-amino-2-carboxy-ethyl)-phenyl]- 4-methoxy-3-pyrrolin-2-one-hydrochloride
(48) 3-(4-amidinophenyl)-1-[4-(2-carboxy- 2-hydroxyethyl)-phenyl]-4-methoxy-3-pyrrolin-2-one-hydrochloride
(49) 1-[4-(1-aminoethyl)-phenyl]-3-[4-( 2-carboxy-ethyl)phenyl]-3-pyrrolidin-2-one-hydrochloride
(50) 1-(4-aminomethyl-cyclohexyl)-3-[4-( 2-carboxy-ethyl)-phenyl]-4-methoxy-3-pyrrolin-2-one-hydrochloride
(51) 1-[4-(1-amino-1-methyl-ethyl)-phenyl]-3-[4-( 2-carboxy-ethyl)-phenyl]-4-methoxy-3-pyrrolin-2-one-hydrochloride
(52) 1-(1-amino-1,2,3,4-tetrahydro-naphth-6-yl)-3-[4-(2-carboxy-ethyl)-phenyl]-4-methoxy-3-pyrrolin-2-one-hydrochloride
(53) 1-(1-amino-indan-5-yl)-3-[4-( 2-carboxy-ethyl)phenyl] -4-methoxy-3-pyrrolin-2-one-hydrochloride
(54) 1-[3-(2-aminoethyl)-phenyl]-3-[4-( 2-carboxy-ethyl)phenyl]-4-methoxy-3-pyrrolin-2-one-hydrochloride
(55) 1-(4-aminomethyl-phenyl)-3-[4-( 2-carboxy-ethyl)phenyl]-4-methoxy-3-pyrrolin-2-one-hydrochloride Mass spectrum: $(M+H)^+=367$
$R_f$-value: 0.24 (silica gel; methylene chloride/methanol/ conc. ammonia= 4:1:0.25)

(56) 1-[4-(allyloxycarbonyl-amidino)-phenyl]-3-[4-( 2-carboxy-ethyl)-phenyl]-4-methoxy-3-pyrrolin-2-one-hydrochloride
(57) 1-[4-(allyloxycarbonyl-amidino)-phenyl]-3-[4-( 2-carboxy-ethyl)-phenyl]-4-morpholino-3-pyrrolin-2-one-hydrochloride
(58) 1-(4-aminomethyl-phenyl)-3-[4-( 2-carboxy-ethyl)phenyl]-pyrrolidin-2-one-hydrochloride Mass spectrum: $M^+=338$
$R_f$ value: 0.32 (silica gel; methylene chloride/methanol/ conc. ammonia= 4:1:0.25)

(59) 3-[4-(3-carboxy-propyl)-phenyl]-4-methoxy- 1-piperid-4-yl-3-pyrrolin-2-one-hydrochloride
(60) 1-(4-amidinophenyl)-3-[4-(2-carboxy-ethyl)-phenyl]-4-(morpholinocarbonyl-methoxy)-3-pyrrolin-2-one-hydrochloride
(61) 1-[4-(2-acetylamino-2-carboxy-ethyl)-phenyl]-3-(4-amidinophenyl)-4-methoxy-3-pyrrolin-2-one-hydrochloride
(62) 3-(4-amidinophenyl)-1-[4-[2-carboxy- 2-(methanesulphonyl-amino)-ethyl]-phenyl]-4-methoxy-3-pyrrolin-2-one-hydrochloride

EXAMPLE 3

1-(1-Amidinoperid-4-yl)-4-methoxy-3-[4-(2-methoxycarbonyl-ethyl)-phenyl]-3-pyrrolin-2-one Prepared from 4-methoxy-3-[4-(2-methoxycarbonyl-ethyl)phenyl]- 1-(piperid-4-yl)-3-pyrrolin-2-one and S-ethyl-isothiourea-hydrobromide by heating to 100° C. for 4 hours in dimethylformamide in the presence of sodium carbonate.

EXAMPLE 4

1-[4-(1-Aminoethyl)-phenyl]-3-[4-(2-methoxycarbonyl-ethyl)-phenyl]-pyrrolidin-2-one Prepared from 1-[4-[1-[(tert.butyloxycarbonyl)-amino] ethyl]-phenyl]- 3-[4-(2-methoxycarbonyl-ethyl)-phenyl]-pyrrolidin- 2-one by stirring for 2 hours in a 1:1 mixture of methylene chloride and trifluoroacetic acid.

The following compounds are obtained analogously:
(1) 1-[4-aminomethyl-cyclohexyl]-4-methoxy-3-[4-(2-methoxy-carbonyl-ethyl)-phenyl]-3-pyrrolin-2-one (2) 1-[4-(1-amino-1-methyl-ethyl)-phenyl]-4-methoxy-3-[4-(2-methoxycarbonyl-ethyl)-phenyl]-3-pyrrolin-2-one
(3) 1-[1-amino-1,2,3,4-tetrahydro-naphth-6-yl]- 4-methoxy-3-[4-(2-methoxycarbonyl-ethyl)-phenyl]- 3-pyrrolin-2-one
(4) 1-[1-amino-indan-5-yl]-4-methoxy-3-[4-( 2-methoxycarbonyl-ethyl)-phenyl]-3-pyrrolin-2-one
5) 1-[3-(2-aminoethyl)-phenyl]-4-methoxy-3-[4-( 2-methoxycarbonyl-ethyl)-phenyl]-3-pyrrolin-2-one
(6) 4-methoxy-3-[4-(3-methoxycarbonyl-propyl)-phenyl]-1-piperid-4-yl-3-pyrrolin-2-one

EXAMPLE 5

1-(4-Aminomethyl-phenyl)-3-[4-(2-methoxycarbonyl-ethyl)phenyl]-pyrrolidin-2-one and 1-(4-Aminomethyl-phenyl)-4-methoxy-3-[4-(2-methoxycarbonyl-ethyl)-phenyl]-3-pyrrolin-2-one A solution of 0.45 g of 1-(4-cyanophenyl)-4-methoxy-3-[4-(2-methoxycarbonyl-ethyl)-phenyl]-4-pyrrolin-2-one in 100 ml of absolute methanol and 100 ml of absolute methanol saturated with hydrogen chloride is hydrogenated in the presence of 0.2 g of 10% palladium on activated charcoal under a hydrogen pressure of 5 bar at ambient temperature for 7 hours. Then the catalyst is filtered off and the filtrate is evaporated down under reduced pressure. The residue is dissolved in water and mixed with 1N sodium hydroxide solution. The aqueous phase is extracted twice with ethyl acetate and once with methylene chloride. The combined organic phases are dried and the solvent is evaporated down. The residue remaining is chromatographed over silica gel with methylene chloride/methanol/conc. ammonia (10:1:0.1).

Yield: 100 mg of 1-(4-aminomethyl-phenyl)-3-[4-(2-methoxycarbonyl-ethyl)-phenyl]-pyrrolidin-2-one (24% of theory) (=Compound A), Mass spectrum: M$^+$=352

R$_f$ value: 0.33 (silica gel; methylene chloride/methanol/conc. ammonia= 10:1:0.1)

Yield: 140 mg of 1-(4-aminomethyl-phenyl)-4-methoxy-3-[ 4-(2-methoxycarhonyl-ethyl)-phenyl]-3-pyrrolin-2-one-hydrochloride (31% of theory) (=Compound B), Mass spectrum. M$^+$=380

R$_f$ value: 0.28 (silica gel; methylene chloride/methanol/conc. ammonia= 10:1:0.1)

EXAMPLE 6

4-Methoxy-1-[4-(methoxycarbonyl-amidino)-phenyl]-3-[4-(2-methoxycarbonyl-ethyl)-phenyl]-3-pyrrolin-2-one Prepared from 1-(4-amidinophenyl)-4-methoxy-3-[4-(2-methoxycarbonyl-ethyl)-phenyl]-3-pyrrolin-2-one and methyl chloroformate in methylene chloride with the addition of 0.1N sodium hydroxide solution with vigorous stirring.

The following compounds are obtained analogously:
(1) 4-methoxy-1-[4-(methoxycarbonyl-amidino)-phenyl]-3-[ 4-[2-(isopropoxycarbonyl)-ethyl]-phenyl]-3-pyrrolin-2-one
(2) 1-[4-[[(1-acetyloxy-ethyl)-oxycarbonyl]-amidino]phenyl]- 4-methoxy-3-[4-(2-methoxycarbonyl-ethyl)phenyl]- 3-pyrrolin-2-one Carbonic acid (1-acetyloxy-ethyl)-(4-nitrophenyl)-ester and N-ethyl-diisopropylamine are used.
(3) 1-[4-[[(acetyloxymethyl)-oxycarbonyl]-amidino]phenyl]- 4-methoxy-3-[4-(2-methoxycarbonyl-ethyl)phenyl]- 3-pyrrolin-2-one Carbonic acid acetyloxymethyl-(4-nitrophenyl)-ester and N-ethyl-diisopropylamine are used.
(4) 1-[4-(ethoxycarbonyl-amidino)-phenyl]-4-methoxy-3-[4-(2-methoxycarbonyl-ethyl)-phenyl]-3-pyrrolin-2-one Ethyl chloroformate is used.
(5) 1-[4-(allyloxycarbonyl-amidino)-phenyl]-4-methoxy-3-[4-(2-methoxycarbonyl-ethyl)-phenyl]-3-pyrrolin-2-one Allyl chloroformate is used.
(6) 1-[4-(allyloxycarbonyl-amidino)-phenyl]-3-[4-( 2-methoxy-carbonyl-ethyl)-phenyl]-4-morpholino-3-pyrrolin-2-one Allyl chloroformate is used.
(7) 1-[4-(methoxycarbonyl-amidino)-phenyl]-3-[4-(2-methoxy-carbonyl-ethyl)-phenyl]-4-morpholino-3-pyrrolin- 2-one
(8) 3-[4-(2-ethoxycarbonyl-ethyl)-phenyl]-4-methoxy-1-[4-(methoxycarbonyl-amidino)-phenyl]-3-pyrrolin-2-one

EXAMPLE 7

1-(4-Amidinophenyl)-3-[4-(2-methoxycarbonyl-ethyl)phenyl]-4-(1-oxido-thiomorpholino)-3-pyrrolin-2-one Prepared by the dropwise addition of a solution of iodobenzene-dichloride (1 equivalent) in aqueous pyridine to a stirred solution of 1-(4-amidinophenyl)-3-[ 4-(2-methoxycarbonyl-ethyl)-phenyl]-4-thiomorpholino- 3-pyrrolin-2-one (1 equivalent) in 20% aqueous pyridine at 20° C. with the exclusion of direct sunlight.

The following compound is obtained analogously:
(1) 1-(4-amidinophenyl)-4-methoxy-3-[ 4-(methoxycarbonyl-methylsulphinyl)-phenyl]-3-pyrrolin-2-one

EXAMPLE 8

1-(4-Amidinophenyl)-3-[4-(2-methoxycarbonyl-ethyl)-phenyl]-pyrrolidin-2-one

A solution of 270 mg of 1-(4-amidinophenyl)-3-[4-(2-carboxyethyl)-phenyl]-4-methoxy-3-pyrrolin-2-one-hydrochloride in 180 ml of absolute methanol and 10 ml of absolute methanol saturated with hydrogen chloride is hydrogenated in the presence of 100 mg of 10% palladium on activated charcoal under a hydrogen pressure of 5 bar at ambient temperature for 2.5 hours. A further 100 mg of 10% palladium on activated charcoal are added and hydrogenation is continued for a further 4 hours. Then the catalyst is filtered off and the filtrate is evaporated down under reduced pressure. The residue is dissolved in water and mixed with 1N sodium hydroxide solution. The aqueous phase is extracted three times with methylene chloride, the organic phase is dried and the solvent is evaporated down. The residue remaining is chromatographed over silica gel with methylene chloride/methanol/conc. ammonia (4:1:0.25).

Yield: 120 mg (49% of theory),

Mass spectrum: (M+H)$^+$=366

R$_f$ value: 0.29 (silica gel; methylene chloride/methanol/conc. ammonia= 2:1:0.25)

EXAMPLE 9

1-(4-Amidinophenyl)-3-[4-[ 2-(cyclohexyloxycarbonyl)ethyl]-phenyl]-4-methoxy-3-pyrrolin-2-one-hydrochloride Prepared by passing dry hydrogen chloride through a solution of 1-(4-amidinophenyl)-3-[4-( 2-carboxy-ethyl)phenyl]- 4-methoxy-3-pyrrolin-2-one and an excess of cyclohexanol in methylene chloride for one hour and subsequently heating to 40° C. for one hour.

The following compounds are obtained analogously:
(1) 1-(4-amidinophenyl)-3-[4-[2-[( 2-morpholino-ethyl)oxycarbonyl]-ethyl]-phenyl]-3-pyrrolin- 2-one-hydrochloride 2-Morpholino-ethanol is used.
(2) 1-(4-amidinophenyl)-3-[4-[ 2-(isopropoxycarbonyl)ethyl]-phenyl]-4-methoxy- 3-pyrrolin-2-one-hydrochloride The reaction is carried out in isopropanol.
(3) 1-(4-amidinophenyl)-3-[4-[ 2-(benzyloxycarbonyl)ethyl]-phenyl]-4-methoxy-3-pyrrolin- 2-one-hydrochloride The reaction is carried out in benzyl alcohol.
(4) 1-(4-amidinophenyl)-3-[4-[ 2-(ethoxycarbonyl)-ethyl] phenyl]-4-methoxy-3-pyrrolin- 2-one-hydrochloride The reaction is carried out in ethanol.

EXAMPLE 10

1-[4-(Allyloxycarbonyl-amidino)-phenyl]-4-methoxy-3-[4-[2-[(pivaloyloxymethyl)-oxycarbonyl]-ethyl]-phenyl]- 3-pyrrolin-2-one Prepared by stirring a suspension of 1-[ 4-(allyloxycarbonyl-amidino)-phenyl]-3-[4-( 2-carboxy-ethyl)-phenyl]-4-methoxy-3-pyrrolin-2-one, 2 equivalents of chloromethyl pivalate, 2 equivalents of potassium iodide, 2 equivalents of potassium hydrogen carbonate and 2 equivalents of potassium carbonate in dimethylformamide at ambient temperature for three days.

The following compounds are obtained analogously:
(1) 1-[4-(allyloxycarbonyl-amidino)-phenyl]-3-[4-[ 2-[[-1 [(ethoxycarbonyl)-oxy]-ethyl]-oxycarbonyl]-ethyl]phenyl]- 4-methoxy-3-pyrrolin-2-one The reaction is carried out with 1-(ethoxycarbonyloxy)ethylchloride in dimethylsulphoxide.
(2) 1-[4-(allyloxycarbonyl-amidino)-phenyl]-3-[4-[ 2-[[1-[(cyclohexyloxycarbonyl)-oxy]-ethyl]-oxycarbonyl] ethyl]-phenyl]- 4-morpholino-3-pyrrolin-2-one The reaction is carried out with 1-(cyclohexyloxycarbonyloxy)-ethyl-chloride in dimethylsulphoxide.
(3) 1-[4-(allyloxycarbonyl-amidino)-phenyl]-4-morpholino-3-[4-[2-[(pivaloyloxymethyl)-oxycarbonyl]ethyl]-phenyl]- 3-pyrrolin-2-one

EXAMPLE 11

1-[4-(Allyloxycarbonyl-amidino)-phenyl]-3-[4-[2-[[(dimethylaminocarbonyl)-methyl]-oxycarbonyl]-ethyl]phenyl]-4-methoxy-3-pyrrolin-2-one Prepared by stirring a suspension of 1-[ 4-(allyloxycarbonyl-amidino)-phenyl]-3-[4-[ 2-carboxy-ethyl-phenyl]-4-methoxy-3-pyrrolin-2-one, 1 equivalent of 2-chloro-N,N-dimethylacetamide, 1 equivalent of triethylamine and 0.1 equivalent of sodium iodide in absolute dimethylformamide at ambient temperature for 16 hours.

The following compounds are obtained analogously:
(1) 1-[4-(allyloxycarbonyl-amidino)-phenyl]-4-methoxy-3-[4-[2-[[(morpholinocarbonyl)-methyl]-oxycarbonyl] ethyl]-phenyl]- 3-pyrrolin-2-one 1-(2-chloroacetyl)-morpholine is used.
(2) 1-[4-(allyloxycarbonyl-amidino)-phenyl]-3-[4-[2-[[[(dimethylaminocarbonyl)-methyl]-oxycarbonyl]-ethyl] phenyl]- 4-morpholino-3-pyrrolin-2-one
(3) 1-[4-(allyloxycarbonyl-amidino)-phenyl]-4-morpholino-3-[4-[2-[[(morpholinocarbonyl)-methyl]oxycarbonyl]-ethyl]-phenyl]- 3-pyrrolin-2-one 1-(2-chloroacetyl)-morpholine is used.

EXAMPLE 12

1-(4-Amidinophenyl)-4-methoxy-3-[4-[2-[(pivaloyloxymethyl)-oxycarbonyl]-ethyl]-phenyl]-3-pyrrolin-2-one Prepared by dropwise addition of 1 equivalent of morpholine to 1-[4-(allyloxycarbonyl-amidino)-phenyl]-4-methoxy- 3-[4-[2-[(pivaloyloxymethyl)-oxycarbonyl]ethyl] -phenyl]- 3-pyrrolin-2-one and 0.1 equivalents of tetrakis-(triphenyl-phosphine)-palladium(O) in tetrahydrofuran under inert gas followed by 1 hours' stirring at ambient temperature.

The following compounds are obtained analogously:
(1) 1-(4-amidinophenyl)-3-[4-[2-[[ 1-[(ethoxycarbonyl)oxy] -ethyl]-oxycarbonyl]-ethyl]-phenyl]-4-methoxy- 3-pyrrolin-2-one
(2) 1-(4-amidinophenyl)-3-[4-[2-[ [(dimethylaminocarbonyl)-methyl]-oxycarbonyl]-ethyl]phenyl]- 4-methoxy-3-pyrrolin-2-one
(3) 1-(4-amidinophenyl)-4-methoxy-3-[4-[ 2[[(morpholinocarbonyl)-methyl]-oxycarbonyl]-ethyl]phenyl]- 3-pyrrolin-2-one
(4) 1-(4-amidinophenyl)-3-[4-[2-[ [(dimethylaminocarbonyl)-methyl]-oxycarbonyl]-ethyl]phenyl]- 4-morpholino-3-pyrrolin-2-one
(5) 1-(4-amidinophenyl)-4-morpholino-3-[4-[2-[ [(morpholino-carbonyl)-ethyl]-oxycarbonyl]-ethyl]phenyl]- 3-pyrrolin-2-one
(6) 1-(4-amidinophenyl)-3-[4-[2-[[ 1-[(cyclohexyloxycarbonyl)-oxy]-ethyl]-oxycarbonyl]ethyl]-phenyl]- 4-morpholino-3-pyrrolin-2-one
(7) 1-(4-amidinophenyl)-4-morpholino-3-[4-[2-[ (pivaloyloxy-methyl)-oxycarbonyl]-ethyl]-phenyl]-3-pyrrolin-2-one

EXAMPLE 13

1-(4-Amidinophenyl)-3-[4-(2-carboxy-ethyl)-phenyl]-3-methyl-pyrrolidin-2,4-dione-hydrochloride A solution of 190 mg of 1-(4-amidinophenyl)-3-[4-(2-methoxycarbonyl-ethyl)-phenyl]-3-methyl-pyrrolidin-2,4-dione in 200 ml of 6N hydrochloric acid is stirred for 4 hours at ambient temperature. The precipitate is removed by suction filtering, washed with a little water and dried (yield: 60 mg).

The filtrate is evaporated down, the crystalline residue is triturated-with water, suction filtered and dried (yield: 60 mg).

Total yield: 120 mg (65% of theory), Mass spectrum: $(M+H)^+=380$

Melting point: 275°–280° C.

$R_f$ value: 0.14 (silica gel; methylene chloride/methanol/conc. ammonia= 2:1:0.25)

The following compounds are obtained analogously:
(1) 1-(4-amidinophenyl)-3-[4-(2-carboxy-ethyl)-phenyl]-3-(morpholinocarbonyl-methyl)-pyrrolidin-2,4-dionehydrochloride
(2) 1-(4-amidinophenyl)-3-benzyl-3-[4-( 2-carboxyethyl)phenyl]-pyrrolidin-2,4-dione-hydrochloride

EXAMPLE 14

Dry ampoule containing 2.5 mg of active substance per 1 ml

Composition:

| | |
|---|---|
| Active substance | 2.5 mg |
| Mannitol | 50.0 mg |
| Water for injections ad | 1.0 ml |

Preparation

The active substance and mannitol are dissolved in water. After transferring the solution to the ampoule, it is freeze-dried.

At the point of use, the solution is made up with water for injections.

EXAMPLE 15

Dry ampoule containing 35 mg of active substance per 2 ml

Composition:

| | |
|---|---|
| Active substance | 35.0 mg |
| Mannitol | 100.0 mg |
| Water for injections ad | 2.0 ml |

Preparation

The active substance and mannitol are dissolved in water. After transferring the solution to the ampoule, it is freeze-dried.

At the point of use, the solution is made up with water for injections.

EXAMPLE 16

Tablet containing 50 mg of active substance

Composition:

| | |
|---|---|
| (1) Active substance | 50.0 mg |
| (2) Lactose | 98.0 mg |
| (3) Corn starch | 50.0 mg |
| (4) Polyvinylpyrrolidone | 15.0 mg |
| (5) Magnesium stearate | 2.0 mg |
| | 215.0 mg |

Preparation (1), (2) and (3) are mixed together and granulated with an aqueous solution of (4). (5) is added to the dried granules. From this mixture, compressed tablets are produced, biplanar, facetted on both sides and notched on one side. Diameter of tablets: 9 mm.

EXAMPLE 17

Tablet containing 350 mg of active substance

Composition:

| | |
|---|---|
| (1) Active substance | 350.0 mg |

-continued

Tablet containing 350 mg of active substance

Composition:

| | |
|---|---|
| (2) Lactose | 136.0 mg |
| (3) Corn starch | 80.0 mg |
| (4) Polyvinylpyrrolidone | 30.0 mg |
| (5) Magnesium stearate | 4.0 mg |
| | 600.0 mg |

Preparation (1), (2) and (3) are mixed together and granulated with an aqueous solution of (4). (5) is added to the dried granules. From this mixture, compressed tablets are produced, biplanar, facetted on both sides and notched on one side. Diameter of tablets: 12 mm.

EXAMPLE 18

Capsules containing 50 mg of active substance

Composition:

| | |
|---|---|
| (1) Active substance | 50.0 mg |
| (2) Dried corn starch | 58.0 mg |
| (3) Powdered lactose | 50.0 mg |
| (4) Magnesium stearate | 2.0 mg |
| | 160.0 mg |

Preparation (1) is triturated with (3). This triturate is added to the mixture of (2) and (4), with thorough mixing.

This powdered mixture is packed into size 3 hard gelatin oblong capsules in a capsule filling machine.

EXAMPLE 19

Capsules containing 350 mg of active substance

Composition:

| | |
|---|---|
| (1) Active substance | 350.0 mg |
| (2) Dried corn starch | 46.0 mg |
| (3) Powdered lactose | 30.0 mg |
| (4) Magnesium stearate | 4.0 mg |
| | 430.0 mg |

Preparation (1) is triturated with (3). This triturate is added to the mixture of (2) and (4), with thorough mixing.

This powdered mixture is packed into size 0 hard gelatin oblong capsules in a capsule filling machine.

What is claimed is:

1. A 3-Pyrrolin-2-one of the formula Ia

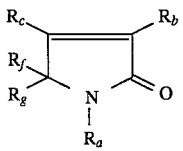

wherein
one of the groups $R_a$ or $R_b$ represents an A—B— group and the other group $R_a$ or $R_b$ represents an F—E—D— group, wherein A represents a $C_{1-4}$-aminoalkyl group or an amidino group, whilst in the above-mentioned aminoalkyl or amidino groups, an amino or imino group may be substituted by an alkyl group or by an ester group of the formulae —CO—OR',
—CO—O—(HCR")—O—CO—R''' and
—CO—O—(HCR")—O—CO—OR''', wherein R' represents a straight-chained or branched $C_{1-6}$-alkyl group, wherein the methyl group may be substituted by a pyridyl, aminocarbonyl, alkylaminocarbonyl, dialkylaminocarbonyl, morpholinocarbonyl, thiomorpholinocarbonyl, 1-oxidothiomorpholinocarbonyl or 1,1-dioxidothiomorpholinocarbonyl group or a $C_{1-3}$-alkyl group may be substituted in the 1-, 2- or 3-position by a phenyl group or in the 2- or 3-position by a morpholino, thiomorpholino, 1-oxidothiomorpholino or 1,1-dioxidothiomorpholino group, or R' may represent an allyl, cycloalkyl or cinnamyl group, R" represents a hydrogen atom or an alkyl group and R"4 represents a straight-chained or branched $C_{1-6}$-alkyl group or a cycloalkyl, cycloalkylalkyl or phenylalkyl group, B represents a phenylene group which may be substituted by a fluorine, chlorine or bromine atom, by an alkyl group, by a trifluoromethyl, hydroxy, alkoxy, alkylsulphenyl, alkylsulphinyl, alkylsulphonyl, $(R_1)_2N$-, N-alkylcarbonyl-$NR_1$- or N-alkanesulphonyl-$NR_1$-, wherein $R_1$ represents a hydrogen atom or an alkyl or phenylalkyl group, or a cycloalkylene group, D represents a phenylene group which may be substituted by a fluorine, chlorine or bromine atom, by an alkyl group, by a trifluoromethyl, hydroxy, alkoxy, alkylsulphenyl, alkylsulphinyl, alkylsulphonyl, $(R_1)_2N$-, N-alkylcarbonyl-$NR_1$-, N-alkanesulphonyl-$NR_1$-, carboxymethoxy or alkoxycarbonylmethoxy group, wherein $R_1$ is as hereinbefore defined, or a cycloalkylene group, E represents a straight-chained or branched $C_{1-5}$-alkylene group optionally substituted by a hydroxy, alkoxy, amino, alkylamino, dialkylamino, alkyl-CO-$NR_1$-, aryl-CO-$NR_1$-, $C_{1-5}$-alkyl-$SO_2$-$NR_1$- or aryl-$SO_2$-$NR_1$- group, wherein $R_1$ is as hereinbefore defined, a straight-chained or branched $C_{2-5}$-alkenylene group, whilst in a $C_{2-4}$-alkylene group, the methylene group linked to the group D may be replaced by an oxygen or sulphur atom or by a sulphinyl, sulphonyl, imino, alkylimino, phenylalkylimino, alkylcarbonylimino, carboxymethylimino or alkoxycarbonylmethylimino group, and F represents a carboxyl group, a sulpho, phosphono, O-alkylphosphono or tetrazol-5-yl group or an ester group of the formulae —CO—OR',
—CO—O—(HCR")—O—CO—R''' and
—CO—O—(HCR")—O—CO—OR''', wherein R', R" and R'''are as hereinbefore defined, $R_c$ represents a hydrogen atom, a $C_{1-5}$-alkyl group, a phenyl group, a hydroxy group, a straight-chained or branched $C_{1-5}$-alkoxy group, whilst a methoxy group may be substituted by a carboxy, alkoxycarbonyl, aminocarbonyl, alkylaminocarbonyl, dialkylaminocarbonyl, piperidinocarbonyl, morpholinocarbonyl, thiomorpholinocarbonyl, 1-oxidothiomorpholinocarbonyl or 1,1-dioxidothiomorpholinocarbonyl group, or $R_c$ represents a phenylalkoxy, alkylamino, dialkylamino, phenylalkylamino, pyrrolidino or piperidino group, whilst the methylene group may be replaced in the 4-position of a piperidino group by an oxygen or sulphur atom or by a sulphinyl, sulphonyl, imino, alkylimino or alkylcarbonylimino group, $R_f$ represents a hydrogen atom, a straight-chained or branched alkyl group or a phenyl group and $R_g$ represents a hydrogen atom or an alkyl group, whilst the alkyl and alkoxy moieties mentioned in the definitions of the above groups may each contain 1 to 3 carbon atoms and the cycloalkyl moieties may each contain 5 or 6 carbon atoms, or a pharmaceutically acceptable salt thereof.

2. A cyclic imino derivative of the formula Ia, according to claim 1, wherein one of the groups $R_a$ or $R_b$ represents an A-B- group and the other group $R_a$ or $R_b$ represents an F-E-D- group, wherein A represents an amino, methyl or amidino group, whilst in the above-mentioned aminomethyl or amidino groups an amino or imino group may be substituted by a methyl group or by an ester group of the formulae —CO—OR',
—CO—O—(HCR")—O—CO—R''' and
—CO—O—(HCR")—O—CO—OR''', wherein R' represents a straight-chained or branched $C_{1-3}$-alkyl group, whilst the methyl group may be substituted by a dimethylaminocarbonyl, piperidinocarbonyl or morpholinocarbonyl group, or R' represents an allyl, phenylmethyl, 2-morpholinoethyl or cyclohexyl group, R" represents a hydrogen atom or a methyl group and R'''represents a straight-chained or branched $C_{1-4}$-alkyl group or a cyclohexyl group, B represents a phenylene group which may be substituted by a methyl group or by a fluorine, chlorine or bromine atom, or a cyclohexylene group, D represents a phenylene group which may be substituted by a fluorine, chlorine or bromine atom or by a methyl, carboxymethoxy or methoxycarbonylmethoxy group, or a cyclohexylene group, E represents a straight-chained or branched $C_{1-4}$-alkylene group optionally substituted by a hydroxy, methoxy, amino, acetylamino or methanesulphonylamino group, whilst in an alkylene group having 2 or 3 carbon atoms the methylene group linked to the group D may be replaced by an oxygen or sulphur atom or by a sulphinyl, sulphonyl, imino, methylimino, carboxymethylimino or methoxycarbonylmethylimino group, or E represents an alkenylene group having 2 or 3 carbon atoms and F represents a carboxyl group or a phosphono, O-methylphosphono or tetrazol-5-yl group or an ester group of the formulae —CO—OR',
—CO—O—(HCR")—O—CO—R''' and
—CO—O—(HCR")—O—CO—OR''', wherein R', R" and R''' are as hereinbefore defined, $R_c$ represents a hydrogen atom, a phenyl group, a hydroxy group, a straight-chained or branched $C_{1-3}$-alkoxy group, a phenylmethoxy, morpholinocarbonylmethoxy, methylamino, dimethylamino, phenylamino, pyrrolidino or piperidino group, wherein the methylene group in the 4-position of a piperidino group may be replaced by an oxygen or sulphur atom or by a sulphinyl, sulphonyl, imino or acetylimino group, $R_f$ represents a hydrogen atom, a methyl group or a phenyl group and $R_g$ represents a hydrogen atom or a methyl group, or a pharmaceutically acceptable salt thereof.

3. A cyclic imino derivative of the formula Ia, according to claim 1, wherein one of the groups $R_a$ or $R_b$ represents an A—B— group and the other group $R_a$ or $R_b$ represents an F—E—D— group, wherein A represents an aminomethyl or amidino group, whilst in the above-mentioned aminomethyl or amidino groups an amino or imino group may be substituted by a methyl group or by an ester group of the formulae —CO—OR',
—CO—O—(HCR")—O—CO—R''' and
—CO—O—(HCR")—O—CO—O''', wherein R' represents a straight-chained or branched $C_{1-3}$-alkyl group, whilst the methyl group may be substituted by a dimethylaminocarbonyl, piperidinocarbonyl or morpholinocarbonyl group, or R' represents a phenylmethyl or cyclohexyl group, R" represents a hydrogen atom or a methyl group and R''' represents a straight-chained or branched $C_{1-4}$-alkyl group or a cyclohexyl group, B represents a phenylene group which may be substituted by a methyl group or by a fluorine, chlorine or bromine atom, D represents a phenylene group which may be substituted by a fluorine, chlorine or bromine atom or by a carboxymethoxy or methoxycarbonylmethoxy group, E represents a straight-chained or branched $C_{1-3}$-alkylene group optionally substituted by a hydroxy, methoxy or amino group, whilst in a $C_{2-3}$-alkylene group the methylene group linked to the group D may be replaced by an oxygen atom, or E represents an ethenylene group and F represents a carboxyl group or an ester group of the formulae —CO—OR',
—CO—O—(HCR")—O—CO—R''' and
—CO—O—(HCR")—O—CO—OR''', wherein R', R" and R''' are as hereinbefore defined, $R_c$ represents a hydrogen atom, a hydroxy group, a straight-chained or branched $C_{1-3}$-alkoxy group, a phenylmethoxy, morpholinocarbonylmethoxy, dimethylamino, pyrrolidino, piperidino or morpholino group, $R_f$ represents a hydrogen atom, a methyl group or a phenyl group and $R_g$ represents a hydrogen atom or a methyl group, or a pharmaceutically acceptable salt thereof.

4. A cyclic imino derivative of the formula Ia, according to claim 1 wherein one of the groups $R_a$ or $R_b$ represents an A—B— group and the other group $R_a$ or $R_b$ represents an F—E—D— group, wherein A represents an aminomethyl or amidino group, B represents a phenylene group, D represents a phenylene group, E represents an ethylene group and F represents a carboxyl group or an R'O-CO- group in which R' is a straight-chained or branched $C_{1-3}$-alkyl group, $R_c$ represents a hydroxy, methoxy, ethoxy or morpholino group, $R_f$ and $R_g$ each represent a hydrogen atom, the stereoisomers thereof, mixtures thereof and the salts thereof.

5. A compound selected from the group consisting of:

(a) 1-(4-amidinophenyl)-3-[4-(2-carboxy-ethyl)-phenyl]-4-methoxy-3-pyrrolin- 2-one, (b) 1-(4-amidinophenyl)-3-[4-(2-carboxy-ethyl)-phenyl]-4-morpholino- 3-pyrrolin-2-one, (c) 1-(4-aminomethyl-phenyl)-3-[4-(2-carboxy-ethyl)-phenyl]-4-methoxy- 3-pyrrolin-2-one, and the pharmaceutically acceptable salts thereof.

* * * * *